United States Patent
Organ et al.

(10) Patent No.: US 7,250,510 B2
(45) Date of Patent: Jul. 31, 2007

(54) TRANSITION METAL COMPLEXES OF N-HETEROCYCLIC CARBENES, METHOD OF PREPARATION AND USE IN TRANSITION METAL CATALYZED ORGANIC TRANSFORMATIONS

(75) Inventors: Michael G. Organ, Burlington (CA); Christopher J. O'Brien, Guelph (CA); Assam (Eric) B. Kantchev, Singapore (SG)

(73) Assignee: Total Synthesis, Ltd., Burlingon, Ontraio (CA)

( * ) Notice: Subject to any disclaimer, the term of this patent is extended or adjusted under 35 U.S.C. 154(b) by 0 days.

(21) Appl. No.: 11/508,334

(22) Filed: Aug. 23, 2006

(65) Prior Publication Data

US 2007/0073055 A1 Mar. 29, 2007

Related U.S. Application Data

(60) Provisional application No. 60/817,343, filed on Jun. 30, 2006, provisional application No. 60/710,869, filed on Aug. 25, 2005, provisional application No. 60/710,487, filed on Aug. 24, 2005.

(51) Int. Cl.
*C07F 15/00* (2006.01)
*B01J 31/00* (2006.01)
*C07C 2/00* (2006.01)
*C07C 45/00* (2006.01)

(52) U.S. Cl. .................. 544/225; 546/2; 548/103; 502/155; 502/167; 585/509; 568/61; 568/319; 568/671

(58) Field of Classification Search ............... 544/225; 546/2; 548/103; 502/155, 167; 585/509; 568/61, 319, 671
See application file for complete search history.

(56) References Cited

U.S. PATENT DOCUMENTS 6,316,380 B1 11/2001 Nolan et al.
2006/0122398 A1* 6/2006 Karch et al. ............... 548/101

OTHER PUBLICATIONS

Romerosa et al., Inorganic Chemistry, vol. 36, No. 17, pp. 3784-3786 (1997).*
Chen et al., Organometallics, vol. 19, No. 24, pp. 5113-5121 (2000).*
Hatanaka et al., Cross-Coupling of Organosilanes with Organic Halides Mediated by Palladium Catalyst and Tris(diethylamino)sulfonium Difluorotrimethylsilicate, J. Org. Chem., 1988, 920-923, 53.
Tamao et al., Selective Carbon-Carbon Bond Formation by Cross-Coupling of Grignard Reagents with Organic Halides. Catalysis by Nickel-Phosphine Complexes, J. Am. Chem. Soc., 1972, 4374-4376, 94(12).

(Continued)

*Primary Examiner*—Porfirio Nazario-Gonzalez
(74) *Attorney, Agent, or Firm*—Rothwell, Figg, Ernst & Manbeck, P.C.

(57) ABSTRACT

The present invention relates to catalysts of transition metal complexes of N-heterocyclic carbenes, their methods of preparation and their use in chemical synthesis. The synthesis, ease-of-use, and activity of the compounds of the present invention are substantial improvements over in situ catalyst generation. Further, the transition metal complexes of N-heterocyclic carbenes of the present invention may be used as precatalysts in metal-catalyzed cross-coupling reactions.

33 Claims, 4 Drawing Sheets

OTHER PUBLICATIONS

Negishi et al., Selective Carbon-Carbon Bond Formation via Transition Metal Catalysis. A Highly Selective Synthesis of Unsymmetrical Biaryls and Diarylmethanes by the Nickel- or Palladium-Catalyzed Reation of Aryl- and Benzylzinc Derivatives with Aryl Halides, J. Org. Chem., 1977, 1821-1823, 42(10).

King et al., Highly General Stereo-, Regio-, and Chemo-selective Synthesis of Terminal and Internal Coujugated Enzynes by the Pd-catalysed Reactions of Alkynytzinc Reagents with Alkenyl Halides, J.C.S. Chem. Comm., 1977, 683-684.

Stille et al., A General, Selective, and Facile Method for Ketone Synthesis from Acid Chlorides and Organotin Compounds Catalyzed by Palladium, J. Am. Chem. Soc., 1978, 3636-3638, 100(11).

Barder et al., J. Am. Chem. Soc., 2005, 4685, 127.

O'Brien et al., Towards the rational design of palladium-N-heterocyclic carbene catalysts by a combined experimental and computational approach, Tetrahedron, 2005, 9723-9735, 61.

Milne et al., An Extremely Active Catalyst for the Negishi Cross-Coupling Reaction, J. Am. Chem. Soc., 2004, 13028-13032, 126(40).

Brenstrum et al., Phosphaadamantanes as Ligands for Palladium Catalyzed Cross-Coupling Chemistry: Library Synthesis, Characterization, and Screening in the Suzuki Coupling of Alkyl Halides and Tosylates Containing β-Hydrogens with Boronic Acids and Alkylboranes, J. Org. Chem., 2004, 7635-7639, 69(22).

Kirchhoff et al., A Method for Palladium-Catalyzed Cross-Couplings of Simple Alkyl Chlorides: Suzuki Reactions Catalyzed by $[Pd_2(dba)_3]/PCy_3$, Angew. Chem. Int. Ed., 2002, 1945-1947, 41(11).

Netherton et al., Suzuki Cross-Couplings of Alkyl Tosylates that Possess β Hydrogen Atoms: Synthetic and Mechanistic Studies, Angew. Chem., 2002, 4066-4068, 114(20).

Grasa et al., Suzuki-Miyaura Cross-Coupling Reactions Medicated by Palladium/Imidazolium Salt Systems, Organometallics, 2002, 2866-2873, 21(14).

Netherton et al., Room-Temperature Alkyl-Alkyl Suzuki Cross-Coupling of Alkyl Bromides that Possess β Hydrogens, J. Am. Chem. Soc., 2001, 10099-10100, 123(41).

Frisch et al., Cross-Coupling Reactions, Angew, Chem. Int. Ed., 2005, 674-688, 44.

Malatesta et al., J. Chem. Soc., 1957, 1186.

Jackstell et al., A Highly Efficient Catalyst for the Telomerization of 1,3-Dienes with Alcohols: First Synthesis of a Monocarbenepalladium(0)—Olefin Complex, Angew. Chem. Int. Ed., 2002, 986-989, 41(6).

Frisch et al., First Kumada reaction of alkyl chlorides using N-heterocyclic carbene/palladium catalyst systems, Journal of Organometallic Chemisty, 2003, 403-409, 687.

Frey et al., Synthesis and Characterization of N-Heterocyclic Carbene Phospha-Palladacycles and Their Properties in Heck Catalysis, Organometallics, 2005, 4416-4426, 24(18).

Gstöttmayr et al., A Defined N-Heterocyclic Carbene Complex for the Palladium-Catalyzed Suzuki Cross-Coupling of Aryl Chlorides at Ambient Temperatures, 2002, 1363-1365, 41(8).

Herrmann et al., Chelating N-heterocyclic carbene ligands in palladium-catalyzed heck-type reactions, Journal of Organometallic Chemistry, 1998, 93-96, 557.

Navarro et al., Synthesis of novel (NHC)Pd(acac)Cl complexes (acac=acetylacetonate) and their activity in cross-coupling reactions, Tetrahedron, 2005, 9716-9722, 61.

Singh et al., Simple (Imidazol-2-ylidene)-Pd-Acetate Complexes as Effective Precatalysts for Sterically Hindered Suzuki-Miyaura Couplings, Org. Lett, 2005, 1829-1832, 7(9).

Lebel et al., Structure and Reactivity of "Unusual" N-Heterocyclic Carbene (NHC) Palladium Complexes Synthesized from Imidazolium Salts, J. Am. Chem. Soc., 2004, 5046-5047, 126(16).

Viciu et al., N-Heterocyclic Carbene Palldium Complexes Bearing Carboxylate Ligands and Their Catalytic Activity in the Hydroarylation of Alkynes, Organometallics, 2004, 3752-3755, 23(15).

Viciu et al., Synthetic and Structural Studies of (NHC)Pd(allyl)Cl Complexes (NHC=N-heterocyclic carbene), Organometallics, 2004, 1629-1635, 23(7).

Viciu et al., Synthesis, Characterization, and Catalytic Activity of N-Heterocyclic Carbene (NHC) Palladacycle Complexes, Org. Lett, 2003, 1479-1482, 5(9).

Jensen et al., A Well-Defined Complex for Palladium-Catalyzed Aerobic Oxidation of Alcohols: Design, Synthesis, and Mechanistic Considerations, Angew. Chem. Int. Ed., 2003. 3810-3813, 42.

Peris et al., Recent homogeneous catalytic applications of chelate and pincer N-heterocyclic carbenes, Coord. Chem., 2004, 2239-2246, 248.

Crudden et al., Stability and reactivity of N-heterocyclic carbene complexes, Coord. Chem., 2004, 2247-2273, 248.

Herrmann et al., Phospha-palladacycles and N-heterocyclic carbene palladium complexes: efficient catalysts for CC-coupling reactions, Journal of Organometallic Chemistry, 2003, 229-248, 687.

Herrmann, W.A., N-Heterocyclic Carbenes: A New Concept in Organometallic Catalysis, Angew. Chem. Int. Ed., 2002, 1290-1309, 41.

Arentsen et al., Tetrahedron Lett., 2004, 3511-3515, 45.

Hadei et al., Electronic Nature of N-heterocyclic Carbene Ligands: Effect on the Suzuki Reaction, Org. Lett., 2005, 1991-1994, 7(10).

Arentsen et al., On the efficiency of two-coordinate palladium (0) N-heterocyclic carbene complexes in amination and Suzuki-Miyaura reactions of aryl chlorides, Tetrahedron, 2005, 9710-9715, 61.

Bertogg et al., Eur. J. Inorg. Chem., 2005, 347-356. (not available).

Marion et al., (IPr)Pd(acac)Cl: An Easily Synthesized, Efficient, and Versatile Precatalyst for C-N and C-C Bond Formation, J. Org. Chem., 2006, 3816-3821, 71(10).

McDougal et al., Asymmetric Morita-Baylis-Hillman Reactions Catalyzed by Chiral Bronsted Acids, J. Am. Chem. Soc., 2003, 12094-12095, 125(40).

Huo, S., Highly Efficient, General Procedure for the Preparation of Alkylzinc Reagents from Unactivated Alkyl Bromides and Chlorides, Org. Lett., 2003, 423-425, 5(4).

* cited by examiner

TRANSITION METAL COMPLEXES OF N-HETEROCYCLIC CARBENES, METHOD OF PREPARATION AND USE IN TRANSITION METAL CATALYZED ORGANIC TRANSFORMATIONS

This application claims the benefit under 35 USC §119(e) from U.S. provisional patent application Ser. No. 60/710,869, filed Aug. 25, 2005, U.S. provisional patent application Ser. No. 60/710,487, filed Aug. 24, 2005 and U.S. provisional patent application Ser. No. 60/817,343, filed Jun. 30, 2006.

FIELD OF THE INVENTION

The present invention relates to catalysts for chemical synthesis, particularly catalysts of transition metal complexes of N-heterocyclic carbenes, their methods of preparation and their use in chemical synthesis.

BACKGROUND OF THE INVENTION

The formation of C—X bonds, where X is for example C, S, N, B, O, Sn and Si, is crucial in chemical synthesis and some of the most powerful methodologies to create these bonds are cross-coupling reactions. Over the last thirty years, the development of transition metal catalyzed cross-coupling reactions has transformed the way these bonds are created (Metal-Catalyzed Cross-Coupling Reactions, 2 ed. [Eds.: A. de Meijere, F. Diederich), Wiley-VCH, Weinheim, (2004); Handbook of Organopalladium Chemistry for Organic Synthesis, ed. (Ed.: E. Negishi), John Wiley & Sons, New York, (2002)].

Within the current arsenal of transition metal catalyzed cross-coupling protocols, palladium processes are amongst the most widely employed and include Hiyama [Y. Hatanaka, T. Hiyama, J. Org. Chem. (1988), 53, 918], Kumada [K. Tamao, K. Sumitani, M. Kumada, J. Am. Chem. Soc. (1972), 94, 4374], Negishi [E. Negishi, A. O. King, N. Okukado, J. Org. Chem. (1977), 42, 1821; A. O. King, N. Okukado, E. Negishi, Chem. Commun. (1977), 683], Suzuki [N. Miyaura, K. Yamada, A. Suzuki, Tetrahedron Lett. (1979), 20, 3437] and Stille [D. Milstein, J. K. Stille, J. Am. Chem. Soc. (1978), 100, 3636] reactions. In spite of tremendous progress in the developments of general methods to couple aryl and alkenyl halides, the use of alkyl halides remained a longstanding challenge, until the advent of bulky, electron rich phosphine ligands. In fact, central to the success of these transformations are palladium metal centers ligated most often with tertiary phosphines or, recently N-heterocyclic carbenes. Unfortunately, phosphines are air sensitive and some even pyrophoric. Furthermore, because active palladium (0) complexes are unstable and normally decompose with time, most protocols involve in situ formation of the catalyst.

Although yearly improvements to the supporting ligands have been made [A. Zapf, M. Beller, Chem. Commun. (2005), 431; T. E. Barder, S. D. Walker, J. R. Martinelli, S. L. Buchwald, J. Am. Chem. Soc. (2005), 127, 4685; C. J. O'Brien, E. A. B. Kantchev, G. A. Chass, N. Hadei, A. C. Hopkinson, M. G. Organ, D. H. Setiadi, T. H. Tang, D. C. Fang, Tetrahedron (2005), 61, 9723; J. E. Milne, S. L. Buchwald, J. Am. Chem. Soc. (2004), 126, 13028; T. Brenstrum, D. A. Gerristma, G. M. Adjabeng, C. S. Frampton, J. Britten, A. J. Robertson, J. McNulty, A. Capretta, J. Org. Chem. (2004), 69, 7635; T. Brenstrum, D. A. Gerristma, G. M. Adjabeng, C. S. Frampton, J. Britten, A. J. Robertson, J. McNulty, A. Capretta, J. Org. Chem. (2004), 69, 7635; J. H. Kirchhoff, C. Dai, G. C. Fu, Angew. Chem. (2002), 114, 2025; Angew. Chem. Int. Ed. (2002), 41, 1945; M. R. Netherton, G. C. Fu, Angew. Chem. (2002), 114, 4066; Angew. Chem. Int. Ed. (2002), 41, 3910; G. A. Grasa, M. S. Viciu, J. Huang, C. Zhang, M. L. Trudell, S. P. Nolan, Organometallics (2002), 21, 2866; M. R. Netherton, C. Dai, K. Neuschütz, G. C. Fu, J. Am. Chem. Soc. (2001), 123, 10099], advanced ligands [A. C. Frisch, M. Beller, Angew. Chem. (2005), 117, 680; Angew. Chem. Int. Ed. (2005), 44, 674] are still under-used mainly due to sensitivity, difficulty-of-use, limited availability and expense. Indeed, most synthetic chemists still rely on the reasonably versatile Pd(PPh$_3$)$_4$, first synthesized by Malatesta and Angoletta in 1957 [L. Malatesta, M. Angoletta, J. Chem. Soc. (1957), 1186].

As mentioned above, recently, an alternative to the "tried and tested" phosphine ligands has emerged. N-Heterocyclic carbenes (NHC) have attracted considerable interest as ligands for transition metal homogeneous catalysis. Due to their excellent α-donor properties and their variable steric bulk, NHC ligands impart excellent activity and thermal stability to the catalysts formed. The groups of Beller [R. Jackstell, M. G. Andreu, A. C. Frisch, K. Selvakumar, A. Zapf, H. Klein, A. Spannenberg, D. Röttger, O. Briel, R. Karch, M. Beller, Angew. Chem. (2002), 114, 1028; Angew. Chem. Int. Ed. (2002), 41, 986; A. C. Frisch, F. Rataboul, A. Zapf, M. Beller, J. Organomet. Chem. (2003), 687, 403], Herrmann [G. D. Frey, J. Schütz, E. Herdtweck, W. A. Herrmann, Organometallics (2005), 24, 4416; C. W. K. Gstöttmayr, V. P. W. Böhm, E. Herdtweck, M. Grosche, W. A. Herrmann, Angew. Chem. (2002), 114, 1421; Angew. Chem. Int. Ed. (2002), 41, 1363; W. A. Herrmann, C.-P. Reisinger, M. Spiegler, J. Organomet. Chem. (1998), 557, 93], Nolan [O. Navarro, N. Marion, N. M. Scott, J. Gonzalez, D. Amoroso, A. Bell, S. P. Nolan, Tetrahedron (2005), 61, 9716; R. Singh, M. S. Viciu, N. Kramareva, O. Navarro, S. P. Nolan, Org. Lett. (2005), 7, 1829; H. Lebel, M. K. Janes, A. B. Charette, S. P. Nolan, J. Am. Chem. Soc. (2004), 126, 5046; M. S. Viciu, E. D. Stevens, J. L. Petersen, S. P. Nolan, Organometallics (2004), 23, 3752; M. S. Viciu, O. Navarro, R. F. Germaneau, R. A. Kelly III, W. Sommer, N. Marion, E. D. Stevens, C. Luigi, S. P. Nolan, Organometallics (2004), 23, 1629; M. S. Viciu, R. A. Kelly, E. D. Stevens, F. Naud, M. Studer, S. P. Nolan, Org. Lett. (2003), 5, 1479] and Sigman [D. R. Jensen, M. J. Schultz, J. A. Mueller, M. S. Sigman, Angew. Chem. (2003), 115, 3940; Angew. Chem. Int. Ed. (2003), 42, 3810] have made significant progress towards the development of NHC-based palladium catalysts. However, when compared to processes utilizing phosphine ligands, the development of NHC-based protocols has been less successful. Indeed, palladium-NHC catalysts lack the substrate scope and ease-of-use of their phosphine cousins [Peris, E.; Crabtree, R. H. Coord. Chem. Rev. (2004), 248, 2239-2246; Crudden, C. M.; Allen, D. P. Coord. Chem. Rev. (2004), 248, 2247-2273; Herrmann, W. A.; Öfele, K.; v. Preysing, D.; Schneider, K. S. J. Organomet. Chem. (2003), 687, 229-248; Herrmann, W. A. Angew. Chem., Int. Ed. (2002), 41, 1290-1309]. The high sensitivity of isolated N-heterocyclic carbenes necessitates handling under rigorously anhydrous conditions, typically employing a glovebox. These factors make large scale production using these catalysts unattractive [Arentsen, K.; Caddick, S.; Cloke, F. G. N.; Herring, A. P.; Hitchcock, P. B. Tetrahedron Lett. (2004), 45, 3511-3515; Hadei, N.; Kantchev, E. A. B.; O'Brien, C. J.; Organ, M. G. Org. Lett. (2005), 7, 1991-1994; Arentsen, K.; Caddick, S.; Cloke, F. G. N. Tetrahedron (2005), 61, 9710-9715; Grasa, G. A.; Viciu, M. S.; Huang, J.; Zhang, C.; Trudell, M. L.; Nolan, S. P. Organometallics (2002), 21, 2866-2873]. In situ preparation of active Pd—NHC catalysts has been the dominant strategy to overcome these problems, however such strategies have been plagued with irreproducibility and wide yield variations [O'Brien, C. J.; Kantchev, E. A. B.; Chass, G. A.; Hadei, N.; Hopkinson, A. C.; Organ, M. G.; Setiadi, D. H.; Tang, T.-H.; Fang, D.-C. Tetrahedron (2005), 61, 9723-9735].

Palladium (II) complexes of N-ferrocenyl-substituted N-heterocyclic carbenes have been reported [Bertogg, A.; Camponovo. F.; Togni, A. Eur. J. Inorg. Chem. (2005), 347-356]. In this publication, an intermediate $Pd^{II}$ species comprising a pyridine ligand was prepared, however due to its instability and the formation of dimeric species, this compound was converted to a complex containing a triphenylphosphine ligand and this complex was used in catalytic asymmetric amide cyclizations.

There is therefore a need for air-stable, easy-to-prepare-and-handle transition metal-heterocyclic carbene complexes that are readily activated under the reaction conditions for use in routine and industrial chemical synthesis.

SUMMARY OF THE INVENTION

An air and moisture stable N-heterocyclic carbene-Pd(II) precatalyst that generates a monoligated N-heterocyclic carbene-Pd(0) complex in situ has been prepared and shown to be an effective reagent in a variety of cross-coupling reactions. The precatalyst of the present invention comprises a metal species bearing one N-heterocyclic carbene ligand, one or more anionic ligands (depending on the charge of the metal) and a cooperative or throw-away ligand.

Accordingly, the present invention is directed to transition metal complexes of N-heterocyclic carbenes as precatalysts, their methods of preparation and their use in chemical synthesis.

In an embodiment, the present invention relates to a compound of the formula I:

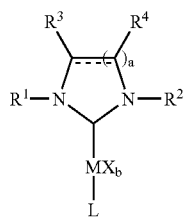

I wherein $R^1$ and $R^2$ are independently or simultaneously selected from the group consisting of $C_{1-20}$alkyl, $C_{3-20}$cycloalkyl, aryl and heteroaryl, said groups being optionally substituted and/or one or more of the $CH_2$ groups in $C_{1-20}$alkyl and/or $C_{3-20}$cycloalkyl is optionally replaced with a heteroatom selected from the group consisting of O, S, and $NR^5$;

$R^3$ and $R^4$ are independently or simultaneously selected from the group consisting of H, halo, $C_{1-20}$alkyl, $OC_{1-20}$alkyl, $C_{3-20}$cycloalkyl, $OC_{3-20}$cycloalkyl, aryl, O-aryl, heteroaryl and O-heteroaryl, said latter 8 groups being optionally substituted and/or one or more of the $CH_2$ groups in $C_{1-20}$alkyl, $OC_{1-20}$alkyl, $C_{3-20}$cycloalkyl and/or $OC_{3-20}$cycloalkyl is optionally replaced with a heteroatom selected from the group consisting of O, S, and $NR^5$;

or $R^3$ and $R^4$ are linked to form an optionally substituted 4 to 12-membered ring system which optionally contains one or more heteroatoms selected from the group consisting of O, S, and $NR^5$;

$R^5$ is selected from the group consisting of H and $C_{1-6}$alkyl;

----- is a single or a double bond;

a is 1, 2 or 3;

M is a transition metal;

b is an integer representing the number of the anionic ligands X required to fulfill the valency requirements of M;

X is an anionic ligand and when b is greater than 1, each X may be the same or different;

L is a 5- or 6-membered optionally substituted N-containing aromatic heterocycle coordinated to M through N, which is optionally benzofused, and/or optionally contains one or more other heteroatoms selected from the group consisting of O, S, and $NR^5$, and/or one or more of the optional substituents on the N-containing aromatic heterocycle is bonded to M in place of one or more X;

or

L is $R^6$—CH=CH—$R^7$ in which $R^6$ and $R^7$ are independently or simultaneously selected from the group consisting of $C_{1-20}$alkyl, $OC_{1-20}$alkyl, $C_{3-20}$cycloalkyl, $OC_{3-20}$cycloalkyl, aryl, O-aryl, heteroaryl and O-heteroaryl, said latter 8 groups being optionally substituted;

one or more of the carbons of the alkyl and cycloalkyl groups of $R^6$ and $R^7$ are optionally replaced with —C(O)—, —C(O)$NR^5$— and —C(O)O—;

aryl is an optionally substituted mono- or polycyclic aromatic radical containing from 6 to 14 carbon atoms;

heteroaryl is a mono- or polycyclic heteroaromatic radical containing from 5 to 14 atoms, of which 1 to 5 atoms may be a heteroatom selected from the group consisting of S, O, N and $NR^5$; and optionally substituted means that one or more of the hydrogens on the group are optionally replaced with halo, OH, $C_{1-6}$alkyl, $OC_{1-6}$alkyl, fluoro-substituted $C_{1-6}$alkyl, fluoro-substituted $OC_{1-6}$alkyl, aryl or aryl that is substituted with 1-5 substituents independently or simultaneously selected from the group consisting of fluoro, $C_{1-4}$alkyl, $OC_{1-4}$alkyl, fluoro-substituted $C_{1-4}$alkyl and fluoro-substituted $OC_{1-4}$alkyl.

The present invention further relates to a method of preparing a compound of formula I wherein X is halo, in particular Cl or Br, the method comprising:

combining a salt of an N-heterocyclic carbene, a ligand L and a metal salt $MX_b$ in the presence of a base to form a reaction mixture; and separating the compound of formula I formed in the reaction mixture;

wherein the N-heterocyclic carbene is

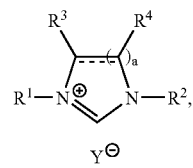

and $R^1$ to $R^4$, M, L and a are defined as above and Y is any suitable anion. It is an embodiment of the present invention that when L is a liquid, no solvent is required for the preparation of compounds of formula I.

Also within the scope of the present invention is a method for performing a metal-catalyzed cross-coupling reaction comprising: contacting suitable cross-coupling substrates with a compound of formula I, under conditions for the formation of cross-coupling product, to form a reaction mixture; and, optionally separating the cross-coupling product from the reaction mixture; wherein the compound of formula I is converted to an active catalyst under suitable reaction conditions in the reaction mixture.

It is an embodiment of the present invention that the ligand "L" is a "cooperative" or "throw-away" ligand which aids or improves the performance of the precatalysts of formula I and/or the corresponding Pd(0) catalyst formed from the formula I compounds. For example, L may act to stabilize the catalyst and/or enhance oxidative addition, transmetalation, reductive elimination and/or diastereo- and/or enantioselectivity during reactions catalyzed by these compounds.

The present invention therefore provides a NHC—Pd(II) precatalyst that can be prepared in large scale and stored with little or no deterioration in performance. Further, when the ligand L is a liquid in the NHC—Pd(II) precatalyst of the present invention, the synthesis of the precatalyst can be performed in solvent-less conditions. The NHC—Pd(II) precatalyst of the present invention can form a monoligated NHC—Pd(0) catalytic complex in situ and provides a clearly defined catalyst for use in subsequent coupling reactions. Another advantage of the present invention is that the activation of the catalyst at a desired temperature can be easily achieved by the choice of ligand L. Further, the performance of the catalyst can be easily altered or tuned by the cooperative ligands. Moreover, the NHC—Pd(0) catalyst generated from the NHC—Pd(II) precatalyst has been found to be an effective reagent in a variety of cross-coupling reactions.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

Figure 1:
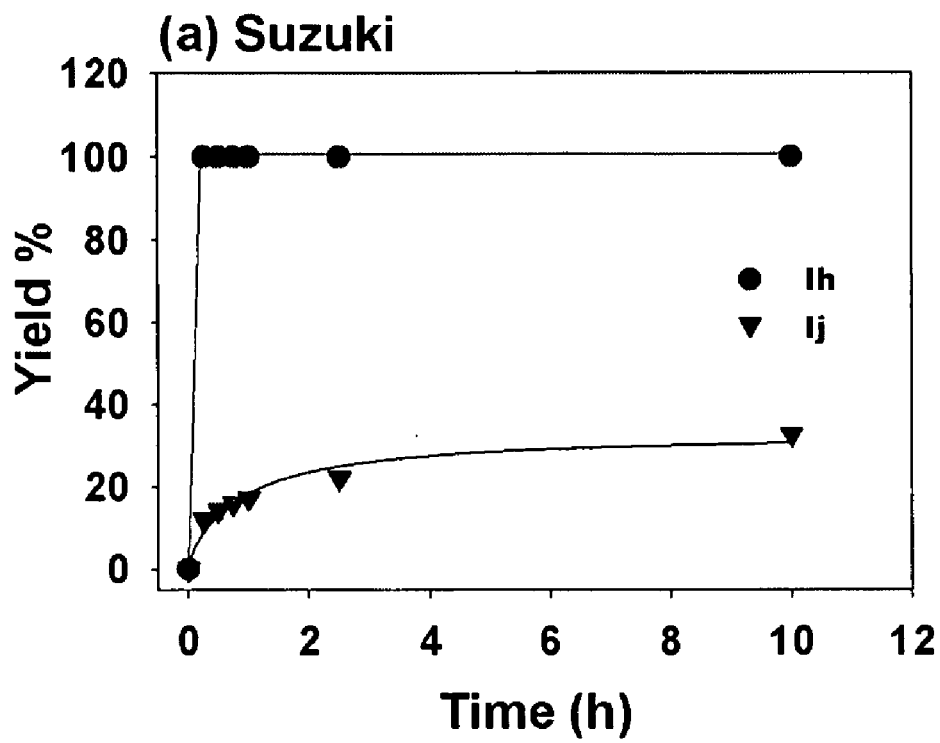
FIG. 1 shows the rate studies with complexes Ih and Ij in the alkyl-alkyl cross-couplings: (a) Suzuki reaction; (b) Negishi reaction.
Figure 1:
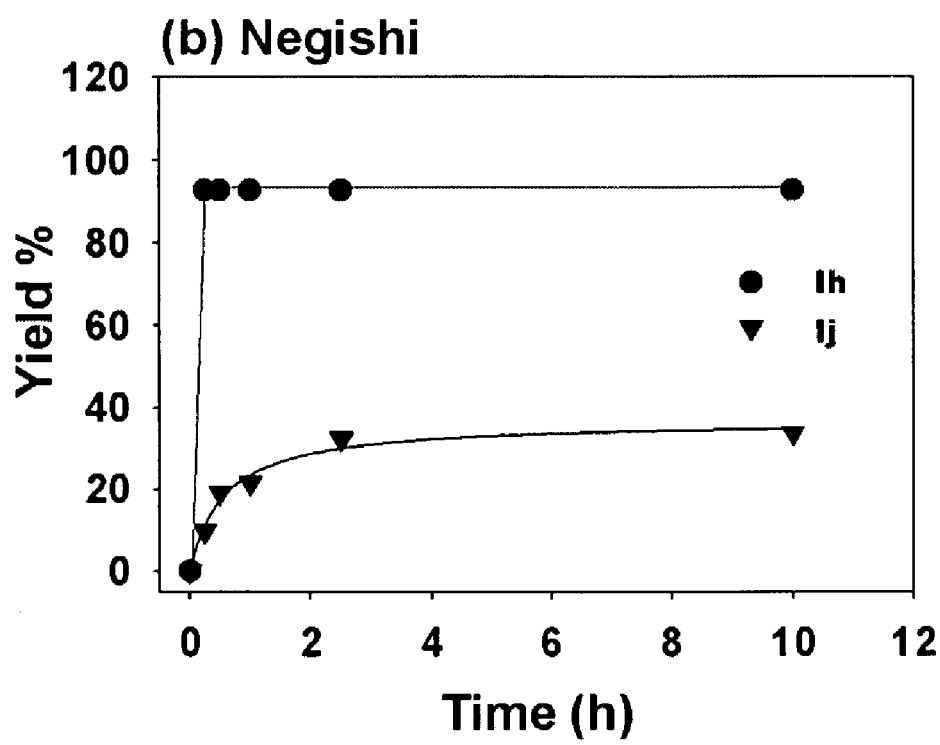

An array of novel Pd-N-heterocyclic carbene complexes have been prepared and shown to have superior properties in the generation of catalysts in transition metal cross-coupling reactions, in particular compared to catalysts generated in situ from corresponding imidazolium salt and a common Pd source ($Pd_2(dba)_3$) (for example as described in S. P. Nolan, U.S. Pat. No. 6,316,380, issued Nov. 13, 2001).

Accordingly, the present invention includes a compound of the formula I:

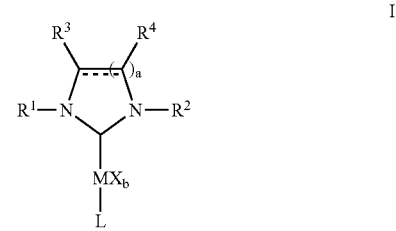

wherein $R^1$ and $R^2$ are independently or simultaneously selected from the group consisting of $C_{1-20}$alkyl, $C_{3-20}$cycloalkyl, aryl and heteroaryl, said groups being optionally substituted and/or one or more of the $CH_2$ groups in $C_{1-20}$alkyl and/or $C_{3-20}$cycloalkyl is optionally replaced with a heteroatom selected from the group consisting of O, S, and $NR^5$;

$R^3$ and $R^4$ are independently or simultaneously selected from the group consisting of H, halo, $C_{1-20}$alkyl, $OC_{1-20}$alkyl, $C_{3-20}$cycloalkyl, $OC_{3-20}$cycloalkyl, aryl, O-aryl, heteroaryl and O-heteroaryl, said latter 8 groups being optionally substituted and/or one or more of the $CH_2$ groups in $C_{1-20}$alkyl, $OC_{1-20}$alkyl, $C_{3-20}$cycloalkyl and/or $OC_{3-20}$cycloalkyl is optionally replaced with a heteroatom selected from the group consisting of O, S, and $NR^5$;

or $R^3$ and $R^4$ are linked to form an optionally substituted 4 to 12-membered ring system which optionally contains one or more heteroatoms selected from the group consisting of O, S, and $NR^5$;

$R^5$ is selected from the group consisting of H and $C_{1-6}$alkyl;

----- is a single or a double bond;

a is 1, 2 or 3;

M is a transition metal;

b is an integer representing the number of the anionic ligands X required to fulfill the valency requirements of M;

X is an anionic ligand and when b is greater than 1, each X may be the same or different;

L is a 5- or 6-membered optionally substituted N-containing aromatic heterocycle coordinated to M through N, which is optionally benzofused, and/or optionally contains one or more other heteroatoms selected from the group consisting of O, S, and $NR^5$, and/or one or more of the optional substituents on the N-containing aromatic heterocycle is bonded to M in place of one or more X;

or

L is $R^6$—CH=CH—$R^7$ in which $R^6$ and $R^7$ are independently or simultaneously selected from the group consisting of $C_{1-20}$alkyl, $OC_{1-20}$alkyl, $C_{3-20}$cycloalkyl, $OC_{3-20}$cycloalkyl, aryl, O-aryl, heteroaryl and O-heteroaryl, said latter 8 groups being optionally substituted;

one or more of the carbons of the alkyl and cycloalkyl groups of $R^6$ and $R^7$ are optionally replaced with —C(O)—, —C(O)$NR^5$— and —C(O)O—;

aryl is an optionally substituted mono- or polycyclic aromatic radical containing from 6 to 14 carbon atoms;

heteroaryl is a mono- or polycyclic heteroaromatic radical containing from 5 to 14 atoms, of which 1 to 5 atoms may be a heteroatom selected from the group consisting of S, O, N and $NR^5$; and optionally substituted means that one or more of the hydrogens on the group are optionally replaced with halo, OH, $C_{1-6}$alkyl, $OC_{1-6}$alkyl, fluoro-substituted $C_{1-6}$alkyl, fluoro-substituted $OC_{1-6}$alkyl, aryl or aryl that is substituted with 1-5 substituents independently or simultaneously selected from the group consisting of fluoro, $C_{1-4}$alkyl, $OC_{1-4}$alkyl, fluoro-substituted $C_{1-4}$alkyl and fluoro-substituted $OC_{1-4}$alkyl.

The term "$C_{1-20}$alkyl" as used herein means substituted or unsubstituted straight and/or branched chain alkyl groups containing from one to twenty carbon atoms and includes methyl, ethyl, propyl, isopropyl, t-butyl, pentyl, hexyl, heptyl, octyl, nonyl, decyl, undecyl, dodecyl, hexadecyl, octadecyl, icosyl and the like.

The term "$C_{3-20}$cycloalkyl" as used herein means saturated cyclic or polycyclic alkyl radicals containing from three to twenty carbon atoms and includes cyclopropyl, cyclobutyl, cyclopentyl, cyclohexyl, cycloheptyl, cyclooctyl, cyclononyl, cyclodecyl, cycloundecyl, cyclododecyl, cyclohexadecyl, cyclooctadecyl, cycloicosyl, adamantyl and the like.

The term "aryl" as used herein means a substituted or unsubstituted monocyclic or polycyclic carbocyclic ring system containing one or two aromatic rings and from 6 to 14 carbon atoms and includes phenyl, naphthyl, anthraceneyl, 1,2-dihydronaphthyl, 1,2,3,4-tetrahydronaphthyl, fluorenyl, indanyl, indenyl and the like.

The term "heteroaryl" as used herein means unsubstituted or substituted mono- or polycyclic heteroaromatic radicals containing from 5 to 14 atoms, of which 1-3 atoms are a heteroatom selected from the group consisting of S, O, N and $NR^{12}$ where $R^{12}$ is H or $C_{1-6}$alkyl, and includes furanyl, thienyl, pyrrolo, pyridyl, indolo, benzofuranyl and the like.

The term "halo" as used herein means halogen and includes chloro, fluoro, bromo, iodo and the like.

The terms "fluoro-substituted $C_{1-6}$alkyl", "fluoro-substituted $OC_{1-6}$alkyl" and "fluoro-substituted aryl" as used herein means that, in the alkyl or aryl portion of these groups, one or more, including all, of the hydrogen atoms are replaced with a fluorine atom.

The term "optionally substituted" as used herein, unless otherwise stated, means that one or more of the hydrogens on the group are optionally replaced with halo, OH, $C_{1-6}$alkyl, $OC_{1-6}$alkyl, fluoro-substituted $C_{1-6}$alkyl, fluoro-substituted $OC_{1-6}$alkyl, aryl or aryl that is substituted with 1-5 substituents independently or simultaneously selected from the group consisting of fluoro, $C_{1-4}$alkyl, $OC_{1-4}$alkyl, fluoro-substituted $C_{1-4}$alkyl and fluoro-substituted $OC_{1-4}$alkyl.

The term "one or more" as used herein means that from one to the maximum allowable substitutions that are allowed.

The present invention includes combinations of groups and substituents that are permitted and would provide a stable chemical entity according to standard chemical knowledge as would be known to those skilled in the art.

The term "polycyclic" or "ring system" as used herein means a cyclic group containing more than one ring in its structure, and includes bicyclic, tricyclic, bridged and spiro ring systems and the like.

It is an embodiment of the invention that the compounds of formula I include those in which $R^1$ and $R^2$ are independently or simultaneously $C_{1-10}$alkyl, $C_{3-16}$cycloalkyl or aryl, wherein the groups are optionally substituted. In an embodiment of the invention, $R^1$ and $R^2$ are independently or simultaneously optionally substituted $C_{3-10}$cycloalkyl or optionally substituted aryl. In another embodiment of the invention, $R^1$ and $R^2$ are independently or simultaneously optionally substituted $C_{4-6}$cycloalkyl or optionally substituted phenyl. In an alternative embodiment of the invention, $R^1$ and $R^2$ are independently or simultaneously optionally substituted cyclopropane, adamantyl or optionally substituted phenyl.

In an embodiment of the invention, $R^3$ and $R^4$ are independently or simultaneously H, $C_{1-10}$alkyl, $C_{3-16}$cycloalkyl or aryl, wherein the latter three groups are optionally substituted. In a further embodiment, $R^3$ and $R^4$ are independently or simultaneously H, optionally substituted $C_{3-10}$cycloalkyl or optionally substituted phenyl. In another embodiment of the invention, $R^3$ and $R^4$ are H. In a still further embodiment of the invention, $R^3$ and $R^4$ are linked to form an optionally substituted 6-membered ring system, such as phenyl.

It is also another embodiment of the invention that a is 1 or 2, specifically 1.

In an embodiment of the invention, M is selected from the group consisting of Fe, Ru, Os, Co, Rh, Ir, Ni, Pd and Pt. In another embodiment of the invention, M is selected from the group consisting of Fe, Ru, Rh, Ir, Pd and Pt. In a further embodiment of the invention, M is Pd, Rh, or Pt. In a still further embodiment of the invention, M is Pd or Pt, suitably Pd.

In an embodiment of the invention, L is selected from the group consisting of pyridine, pyriazine, imidazole, quinoxaline and quinoline, all of which are optionally substituted. In an embodiment of the invention, the optional substituent is electron withdrawing in nature.

In a further embodiment of the invention, L is selected from the group consisting of

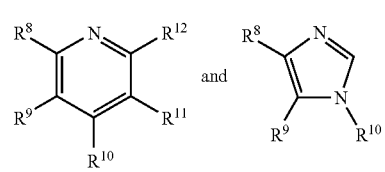

in which $R^8$, $R^9$, $R^{10}$, $R^{11}$ and $R^{12}$ are independently or simultaneously selected from the group consisting of H, halo, OH, $C_{1-6}$alkyl, $OC_{1-6}$alkyl, $C_{3-7}$cylcloalkyl, $OC_{3-7}$cycloalkyl, fluoro-substituted $C_{1-6}$alkyl, fluoro-substituted OC$_{1-6}$alkyl, aryl and aryl that is substituted with 1-5 substituents independently or simultaneously selected from the group consisting of fluoro, C$_{1-4}$alkyl, OC$_{1-4}$alkyl, fluoro-substituted C$_{1-4}$alkyl and fluoro-substituted OC$_{1-4}$alkyl. In a further embodiment of the invention, R$^8$, R$^9$, R$^{10}$, R$^{11}$ and R$^{12}$ are independently or simultaneously selected from the group consisting of H, halo, C$_{1-4}$alkyl, C$_{3-6}$cycloalkyl and aryl. In a still further embodiment of the invention, R$^8$, R$^9$, R$^{10}$, R$^{11}$ and R$^{12}$ are independently or simultaneously selected from the group consisting of H, Br, C$_1$, C$_{1-6}$alkyl, fluoro-substituted C$_{1-6}$alkyl, C$_{5-6}$cycloalkyl and phenyl. In a more particular embodiment of the invention, R$^8$, R$^9$, R$^{10}$, R$^{11}$ and R$^{12}$ are independently or simultaneously selected from the group consisting of H, CH$_3$, CF$_3$, Br, Cl and phenyl. It is another embodiment of the invention that one or more R$^8$, R$^9$, R$^{10}$, R$^{11}$ and R$^{12}$, in particular R$^8$ or R$^{12}$, on the N-containing aromatic heterocycle is bonded to M in place of one or more X.

In an embodiment of the invention, L is

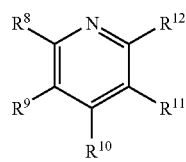

in which the embodiments for R$^8$, R$^9$, R$^{10}$, R$^{11}$ and R$^{12}$ are as defined above.

It is an embodiment of the present invention that the ligand "L" is a "cooperative" or "throw-away" ligand which aids or improves the performance of the precatalysts of formula I and/or the corresponding Pd(0) catalyst formed from the formula I compounds. For example, L may act to stabilize the catalyst and/or enhance oxidative addition, transmetalation, reductive elimination and/or diastereo- and/or enantioselectivity during reactions catalyzed by these compounds.

It is an embodiment of the invention that X is F, Br, Cl, I or OC(O)CH$_3$. It is a more particular embodiment of the invention that X is Cl or Br, suitably Cl. It is a further embodiment of the invention that, when b is greater than one, each of X may be the same or different. For example, when b is 2, one X may be Cl and the other may be Br, or they both may be Cl or Br, suitably Cl.

It is an embodiment of the invention that the optional substituents are selected from halo, C$_{1-6}$alkyl, OC$_{1-4}$alkyl, aryl and aryl that is substituted with 1-5 substituents independently or simultaneously selected from the group consisting of fluoro, C$_{1-4}$alkyl, OC$_{1-4}$alkyl, fluoro-substituted C$_{1-4}$alkyl and fluoro-substituted OC$_{1-4}$alkyl. Further, it is an embodiment of the invention that the optional substituents are selected from F, methyl, ethyl, isopropyl, OCH$_3$, CF$_3$, OCF$_3$, phenyl and phenyl that is substituted with 1-3 substituents, suitably 1-2 substituents, more suitably 1 substituent, independently or simultaneously selected from the group consisting of fluoro, methyl, OCH$_3$, CF$_3$ and OCF$_3$.

In an embodiment of the invention, the compound of formula I is selected from:

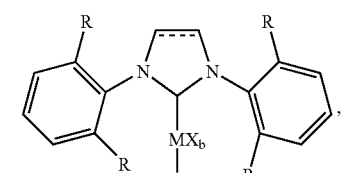
Ia

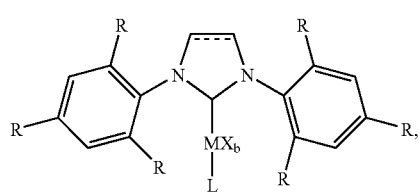
Ib

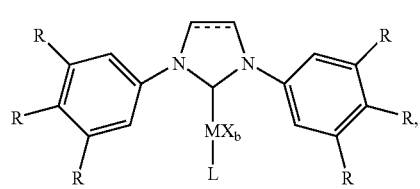
Ic

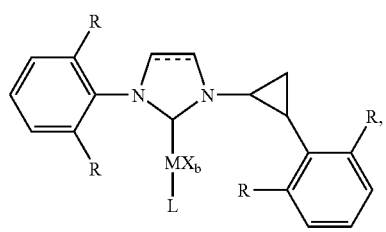
Id

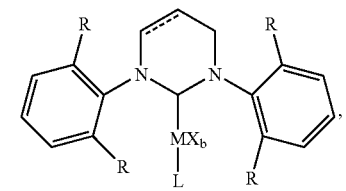
Ie

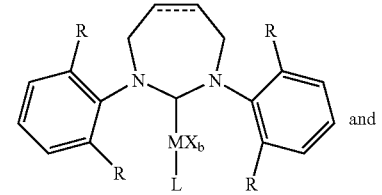
If
and

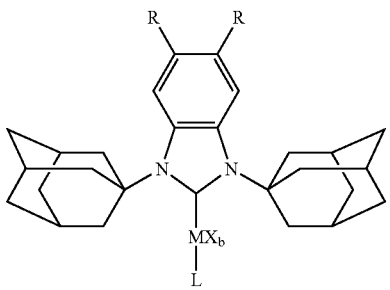
Ig in which R is H, methyl, ethyl, isopropyl, OCH$_3$, CF$_3$, OCF$_3$ or F, and M, X, b, ----and L are as defined above.

In another embodiment of the invention, the compound of formula I is selected from:
Ih
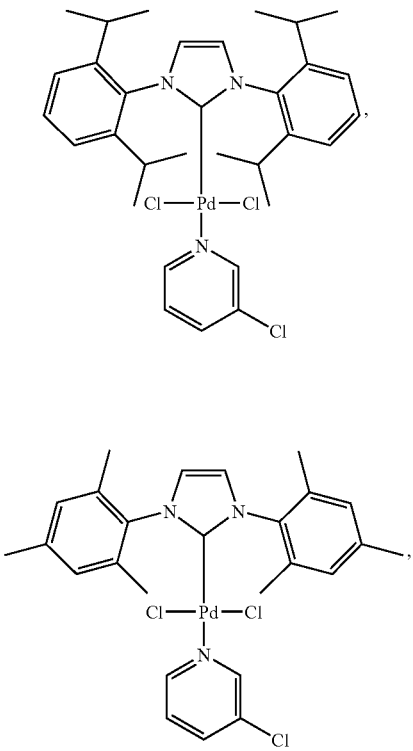
Ii
Ij
Ik
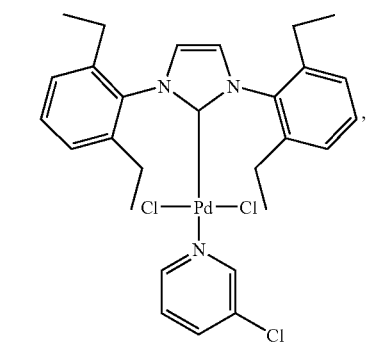
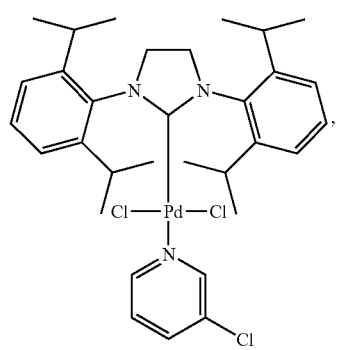
Im
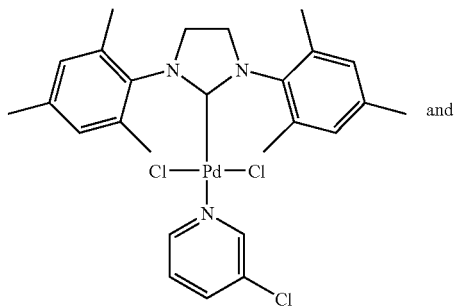
and
In
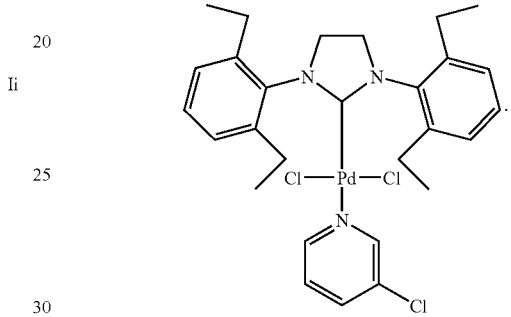
In another embodiment of the invention, the compound of formula I is:
Io
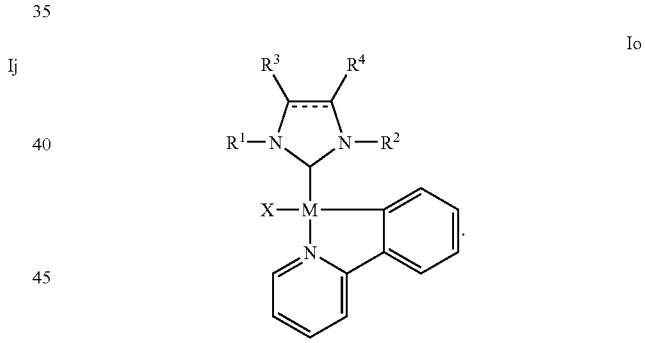
wherein $R^1$, $R^2$, $R^3$, $R^4$, M, ----- and X are as defined in formula I.
In yet another embodiment of the invention, the compound of formula I is:
Ip
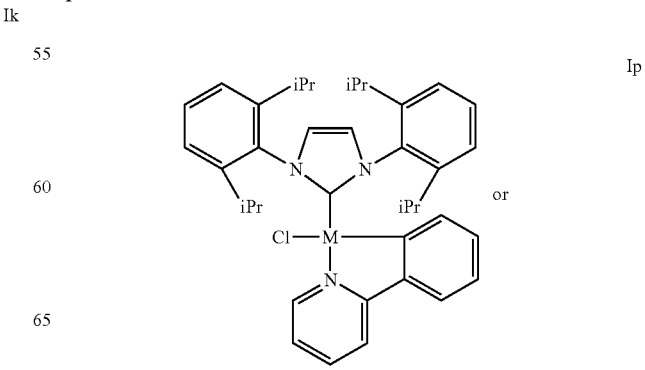
or

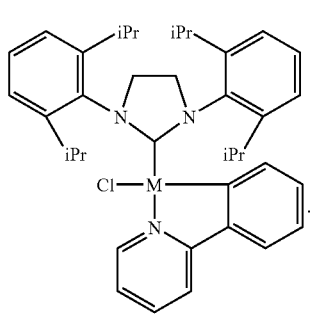

Iq

In accordance with another of its aspects, the present invention includes a method of preparing the compounds of formula I, wherein X is Cl or Br, comprising combining a salt of an N-heterocyclic carbene, a ligand L and a metal salt $MX_b$ in the presence of a base to form a reaction mixture; and separating the compounds of formula I formed in the reaction mixture, wherein the N-heterocyclic carbene is

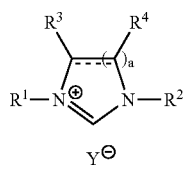

and $R^1$ to $R^4$, L, M, X, ----- and b have the meanings provided above for formula I and Y is any suitable counteranion, such as $F^-$, $Cl^-$, $Br^-$, $I^-$ or $PF_6^-$.

For example, compounds of the invention may be prepared, by the reaction sequence shown in Scheme 1:

Scheme 1

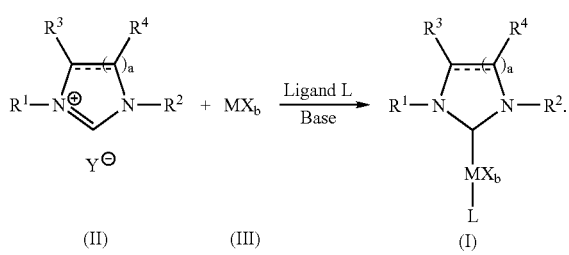

Accordingly, N-heterocyclic carbene salt of formula II in which $R^1$ to $R^4$ and a are as defined in formula I, ----- is a single or double bond (as appropriate) and Y is any suitable counteranion, may be reacted with transition metal complex of formula III in which M and b are as defined in formula I and X is Cl or Br, in the presence of a base and ligand L as defined in formula I, and optionally, a solvent, to provide compounds of formula I. A solvent may not be required when L is a liquid. Advantageously, the reaction may be performed without special precautions to exclude water or oxygen. For example, the reaction may be performed in air. Compounds of formula II, III and L are either commercially available or may be prepared using methods known in the art. The anion Y may be any suitable anion, for example, $F^-$, $Cl^-$, $Br^-$, $I^-$ or $PF_6^-$. The base may be any suitable base which is compatible with the compounds of formula II, III and L. One of ordinary skill in the art would know the appropriate bases which are suitable for use in the formation of compounds of formula I. For example, the base may be $Cs_2CO_3$, $K_2CO_3$, $Na_2CO_3$, $K_3PO_3$, $CaCO_3$ or NaOAc. Suitably, the base is $Cs_2CO_3$, $K_2CO_3$ or $Na_2CO_3$. Compounds of formula II, III and L are suitably reacted in the presence of the base at a temperature of about 40° C. to about 100° C. More suitably, the reaction mixture is conducted at a temperature of about 60° C. to about 80° C. It has been shown that the reaction does not provide optimal yields without the presence of a suitable base. In an embodiment of the invention, the base is present in excess amounts, for example, at least about 1.2 times, suitably at least about 5 times, the amount of the carbene and metal salts. This contrasts with the method of Bertogg et al. [Bertogg, A.; Camponovo. F.; Togni, A. Eur. J. Inorg. Chem. (2005), 347-356] which does not utilize an extra base, like the method of the present invention. The method described in Bertogg also results in the formation of undesirable dimeric side products which make up approximately 50% of the yield from the reaction. The method of the present invention does not produce such undesirable side products and generally provides significantly higher recovery of the desired catalyst precursor, e.g. greater than 70 to 90 percent yield.

For compounds of formula I, wherein X is other than Cl or Br, the method of Bertogg [Bertogg, A.; Camponovo. F.; Togni, A. Eur. J. Inorg. Chem. (2005), 347-356] or Marion et al. [Marion, N.; Ecarnot, E. C.; Navarro, O.; Amoroso, D.; Bell, A.; Nolan, S. P. J. Org. Chem. published on the web Apr. 11, 2006, and references cited therein] may be utilized.

The isolation of the desired compound of the formula I is achieved using standard purification techniques. For example, the compound of formula I is separated from the reaction mixture by purification techniques selected from the group consisting of filtration, recrystallization, extraction, chromatography and combinations thereof.

Also within the scope of the present invention is a method for performing a metal-catalyzed cross-coupling reaction comprising: contacting suitable cross-coupling substrates with a compound of formula I, under conditions for the formation of cross-coupling product, to form a reaction mixture; and, optionally separating the cross-coupling product from the reaction mixture; wherein the compound of formula I is converted to an active catalyst under suitable reaction conditions in the reaction mixture. Typically, suitable reaction conditions include the use of a suitable base, solvent and reaction temperatures as would be well known to those skilled in the art.

The present invention further includes a use of the compounds of formula I in metal catalyzed cross-coupling reactions. The invention also includes a use of the compounds of formula I as a pre-catalyst in a metal-catalyzed cross-coupling reaction.

In an embodiment of the invention, the cross-coupling reaction is for example, but not limited to, a Negishi coupling reaction, a Heck coupling reaction, a Suzuki coupling reaction, a Hiyama coupling reaction, a Sonogashira coupling reaction, a Stille coupling reaction, a Kumada coupling reaction, a Buchwald-Hartwig amination reaction, an allyl substitution reaction, an enolate arylation reaction, a hydroformylation reaction, a carbonylation reaction, a hydrosilylation reaction or a boronylation reaction. Reaction conditions and suitable substrates for all of these reactions would be well known to those skilled in the art. Representative examples are provided in the Experimental section hereinbelow.

In certain embodiments of the invention, the NHC—Pd (II) precatalyst or the NHC—Pd(0) catalyst is covalently tethered to a solid support, such as a polymer bead or a resin. For example, the carbene-containing ligand of the precatalyst or the catalyst of the present invention may be covalently tethered to a solid support, such as a Wang resin. Additionally, one or more of the cross-coupling substrates may be covalently tethered to a solid support, such as a polymer bead or a resin. Further, in certain embodiments, both substrates may be covalently tethered to a solid support. In certain embodiments, one or more of the substrates or the catalyst or the precatalyst are isolated in a semi-permeable membrane, such as a dialysis bag. In certain embodiments of the invention, the catalyst, for example, through the carbene-containing ligand, may be anchored or supported on a catalyst support, including a refractory oxide, such as silica, alumina, titania, or magnesia; or an aluminosilicate clay, or molecular sieve or zeolite, or an organic polymeric resin or sol gel derived monolithic glass.

Also within the scope of the present invention is the use of the compounds of formula I for any organic synthesis, including, for example, library synthesis and drug discovery. For example, the compounds of formula I may be applied in high throughput synthesis of libraries of compounds for use in the screening of compounds for biological testing. The compounds of formula I are compatible with existing high-throughput synthesis methods.

For example, the compounds of formula I may be used in applications for solid-phase synthesis in which multi-step reactions can be performed on resins in continuous flow or batch manner. Still further, the compounds of formula I may be used in applications for solution phase synthesis in which multi-step reactions can be performed in solution with polymer-supported catalysts in continuous flow or batch manner.

Further, the compounds of formula I may be attached to solid supports using methods known in the art and used in chemical transformations in this form as described above. The compounds of formula I may also be used, for example, in the synthesis of natural products, agricultural or pharmaceutical ingredients as single compounds regardless of scale, enantiomeric and diastereomeric purity. The compounds of the present invention may be used in the synthesis of materials for electronic, nanotechnology and medical applications. The term "materials" herein is defined as small molecules, oligomers and polymers as single substances or libraries of substances.

As used herein, the terms "comprises", "comprising", "including" and "includes" are to be construed as being inclusive and open ended, and not exclusive. Specifically, when used in this specification including claims, the terms "comprises", "comprising", "including", "includes" and variations thereof mean the specified features, steps or components that are included. These terms are not to be interpreted to exclude the presence of other features, steps or components.

The following non-limiting examples are illustrative of the invention:

EXPERIMENTAL EXAMPLES

Example 1

Synthesis of the NHC—PdCl$_2$-3-chloropyridine Complexes

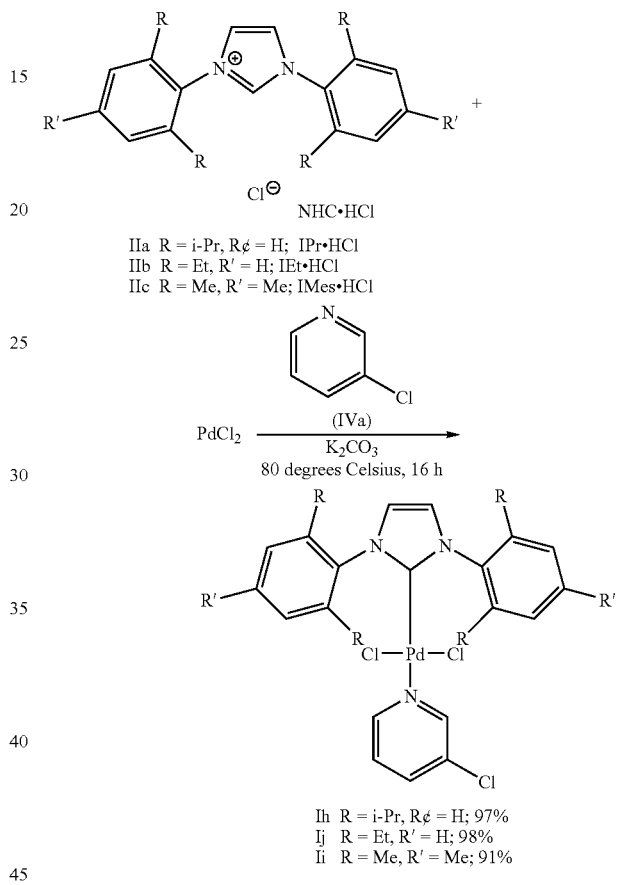

IIa R = i-Pr, R¢ = H; IPr•HCl
IIb R = Et, R' = H; IEt•HCl
IIc R = Me, R' = Me; IMes•HCl

Ih R = i-Pr, R¢ = H; 97%
Ij R = Et, R' = H; 98%
Ii R = Me, R' = Me; 91%

(I) General Synthesis:

In air, a vial was charged with PdCl$_2$ (177 mg, 1.0 mmol), NHC.HCl (1.1 mmol), K$_2$CO$_3$ (691 mg, 5.0 mmol) and a stir bar. 3-Chloropyridine (IVa, 4.0 mL) was added, the vial was capped with a Teflon®-line screw cap and heated with vigorous stirring for 16 hours at 80° C. After cooling to room temperature, the reaction mixture was diluted with CH$_2$Cl$_2$ and passed through a short pad of silica gel covered with a pad of Celite®, eluting with CH$_2$Cl$_2$ until the product was completely recovered. Most of the CH$_2$Cl$_2$ was removed (rotary evaporator) at room temperature, and the 3-chloropyridine was then vacuum-distilled (water aspirator vacuum) and saved for reuse. The pure complexes were isolated after titrating with pentane, decanting of the supernatant and drying in high vacuum.

(i) Complex Ih.

From IPr.HCl, IIa, (468 mg, 1.1 mmol), the complex Ih (677 mg, 97%) was obtained as a yellow solid, mp=240° C. (with decomposition). $^1$H NMR (400 MHz, CDCl$_3$): δ 8.62 (d, J=1.6 Hz, 1H), 8.54 (d, J=5.6 Hz, 1H), 7.57 (d, J=8.2 Hz, 1H), 7.52 (t, J=7.7 Hz, 2H), 7.37 (d, J=7.7 Hz, 4H), 7.16 (s, 2H), 7.09 (dd, J=8.0 Hz, 5.7 Hz, 1H), 3.18 (m, 4H), 1.50 (d, J=6.7 Hz, 12H), 1.14 (d, J=6.8 Hz, 12H). $^{13}$C NMR (100 MHz, CDCl$_3$): δ153.5, 150.5, 149.4, 146.7, 137.4, 135.0, 132.0, 130.3, 125.1, 124.3, 124.1, 28.7, 26.3, 23.2. Anal. Calcd. for C$_{32}$H$_{40}$Cl$_3$N$_3$Pd: C, 56.57; H, 5.93; N, 6.18. Found: C, 56.90; H, 5.99; N, 6.52.

(ii) The above reaction for the preparation of complex Ih was repeated using other bases. The percent yield of Ih was as follows:
Na$_2$CO$_3$—98%
K$_2$CO$_3$—97%
K$_3$PO$_4$—43%
CaCO$_3$—25%
Cs$_2$CO$_3$—93%
NaOAc—60%

It should be noted that reactions performed in the absence of base did not provide optimum amounts of desired products.

(iii) The number of equivalents of base in the above reactions was also varied, with the following results:
2 equiv NaOAc—60% compound Ih
2 equiv K$_2$CO$_3$—80% compound Ih
1.25 and 2.5 equiv. Na$_2$CO$_3$—73% compound Ih (iv) Using the general synthesis in part (i) above, the corresponding Pt complex (R=iPr, R'=H) was made in 60% yield using PtCl$_2$ and K$_2$CO$_3$ as base.

(v) Using the corresponding saturated version of IIa, compound Ik was also prepared:

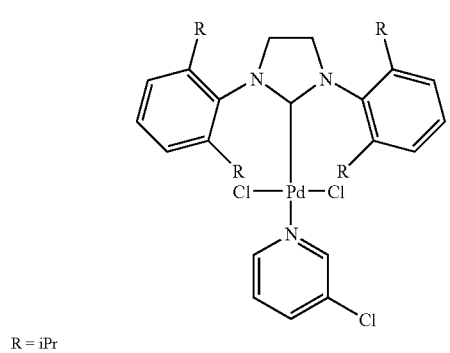

Ik
R = iPr (vi) By replacing 3-chloropyridine with 2-phenyl pyridine, NHC—PdCl-2-phenylpyridine complex Ip was prepared:

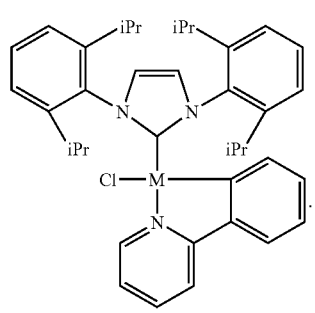

Ip

In air, a vial was charged with PdCl$_2$ (177 mg, 1.0 mmol), NHC.HCl (468 mg, 1.1 mmol), Cs$_2$CO$_3$ (2.3 g, 5.0 mmol) and a stir bar. 2-phenylpyridine (4.0 mL) was added, the vial was capped with a Teflon®-line screw cap and heated with vigorous stirring for 16 h at 80° C. After cooling to room temperature, the reaction mixture was diluted with CH$_2$Cl$_2$ and passed through a short pad of silica gel covered with a pad of Celite, eluting with CH$_2$Cl$_2$ until the product was completely recovered. Most of the CH$_2$Cl$_2$ was removed (rotary evaporator) at room temperature, and the 2-phenylpyridine was then vacuum-distilled (water aspirator) and saved for reuse. The pale yellow complex (480 mg, 70%) was isolated after titrating with pentane, decanting of the supernatant and drying under high vacuum.

Example 2

Catalytic Activity of the NHC—Pd Catalysts Ih, Ii and Ij in alkyl-alkyl Cross-coupling Reactions

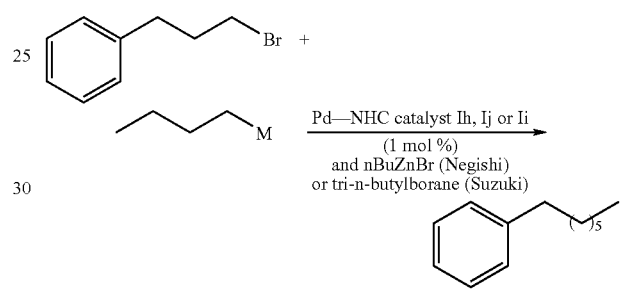

Complex Ih (Example 1, 1 mol %) was subjected to standard alkyl-alkyl Suzuki and Negishi cross-coupling reactions. Reaction conditions are provided in Table 1. The reactions were rapid (Suzuki 5 minutes, Negishi 30 minutes). Quantitative formation of the reaction product was observed at room temperature (Table 1).

Example 3

Rate Studies with Complexes Ih and Ij in alkyl-alkyl Cross-couplings Shown in Example 2

Figure 2:
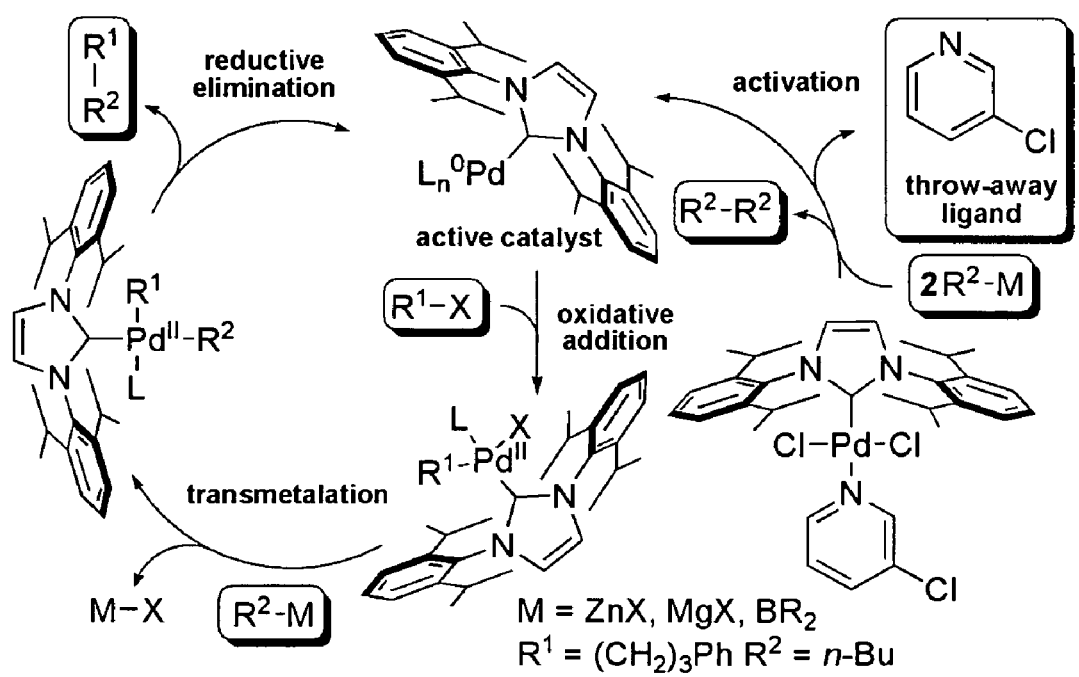
FIG. 2 shows a proposed activation mechanism and use of complex Ih.

The results of the rate studies with complexes Ih and Ij (see Example 1) in the alkyl-alkyl cross-couplings (a) Suzuki reaction, (b) Negishi reaction are shown in FIG. 1. The yields were determined by GC/MS against a calibrated internal standard (undecane). As seen in FIG. 1, the rate of the reaction with complex Ij was much slower than with complex Ih. While not wishing to be limited by theory, these results are suggestive that bulky NHC ligands lead to fast reductive elimination, which suppresses undesired side reactions or catalyst decomposition in a manner analogous with bulky phosphines. Since complexes Ih, Ij and Ii are air- and water tolerant and do not decompose upon standing, heating Ih at 100° C. in DMSO-d$^6$ for 24 hours led to no visable decomposition (by $^1$H and $^{13}$C NMR spectroscopic analysis). Thus, it is unlikely that pyridine dissociation initiates catalyst activation considering the high stability of complex Ih. Rather, rapid reduction facilitated by the organometallic reagent takes place followed by pyridine dissociation from the generated Pd(0) species (FIG. 2).

Example 4

Mechanistic Studies: Activation and Use of Complex Ih

Complex Ih (Example 1) was treated with 2 equivalents of n-heptylzinc bromide and the reaction mixture was analyzed by GC/MS. From this analysis, the formation of n-tetradecane and liberation of 3-chloropyridine was observed. DFT calculations at the B3LYP/DZVP level showed that the binding enthalpy of 3-chloropyridine to NHC-ligated Pd(II) is 4.5 kcal mol$^{-1}$ higher than to Pd(0). Also the dissociation energy of $PH_3$ is 16.5 kcal mol-1 compared to 19.4 kcal mol$^{-1}$ for the 3-chloropyridine.

Example 5

Figure 3:
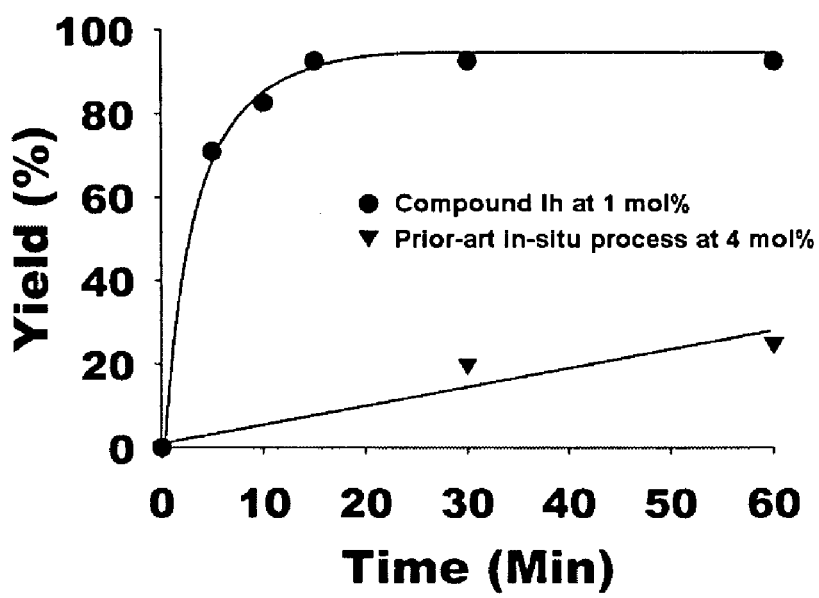
FIG. 3 shows the rate studies with prior art in situ catalyst $Pd_2(dba)_3$/IIa and complex Ih in the alkyl-alkyl Negishi reaction: (a) rate comparison with $Pd_2(dba)_3$/IIa and complex Ih; (b) TON (turnover number) comparison between $Pd_2(dba)_3$/IIa and complex Ih after 1 hour.
Figure 3:
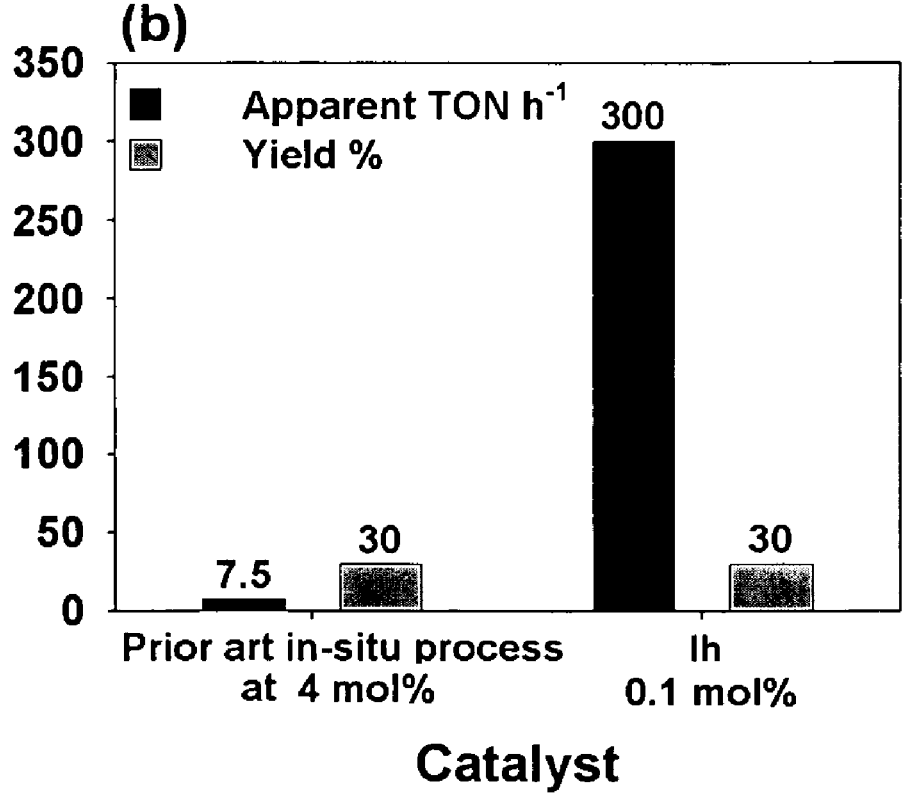
Figure 4:
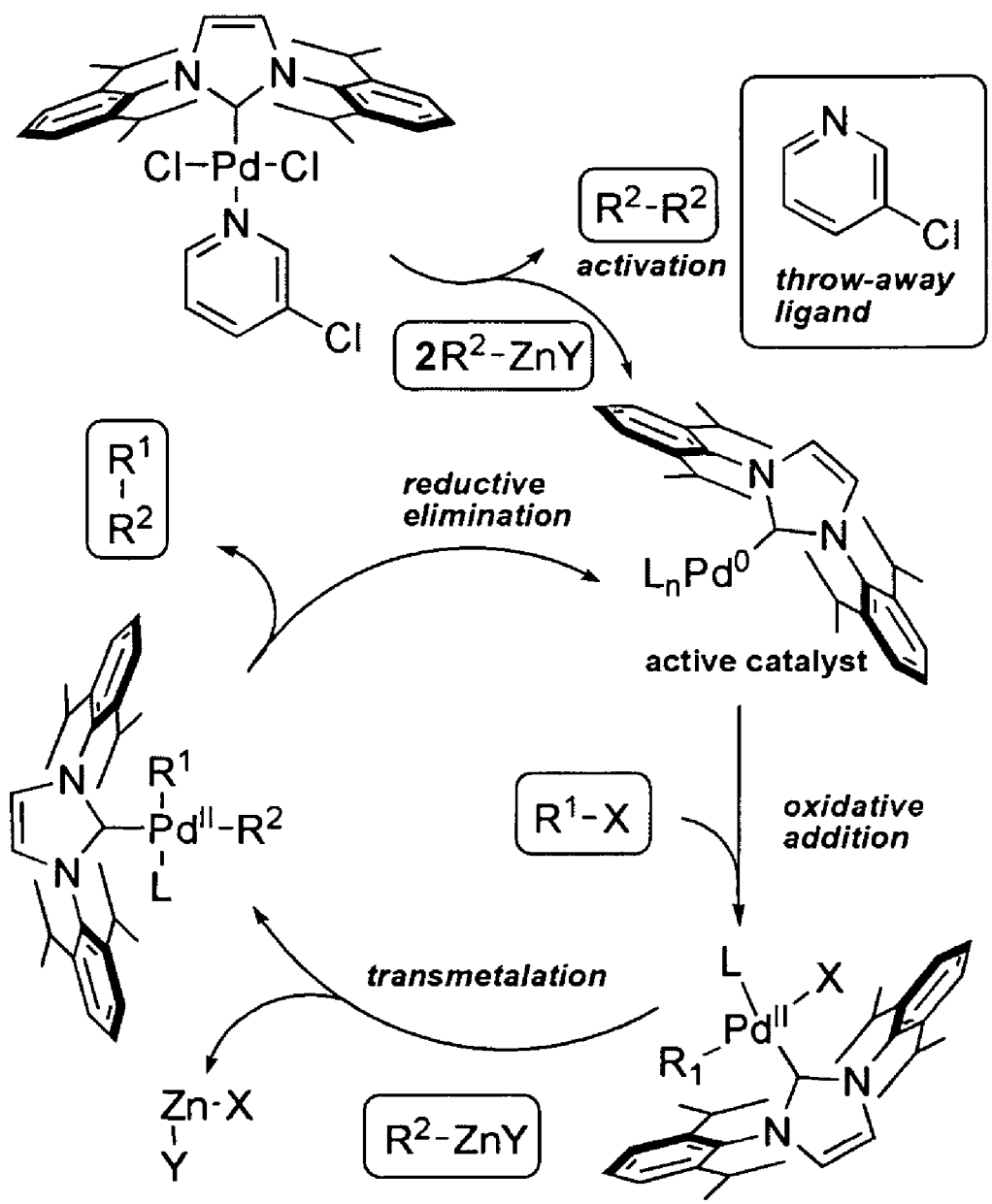
FIG. 4 shows a proposed mechanism for complex Ih catalyzed Negishi cross-coupling reactions.

Comparison Between In Situ Catalyst and NHC—PdCl$_2$-3-chloropyridine (Ih) Complexes in the alkyl-alkyl Negishi Reaction A significant increase in rate was observed when catalysis with complex Ih (Example 1) at 1 mol % was compared to the prior art (for example S. P. Nolan et al., U.S. Pat. No. 6,316,380, Issued Nov. 13, 2001) Pd$_2$(dba)$_3$/IIa in situ protocol at 4 mol % (FIG. 3a). Due to extremely fast rates at 1 mol % of 1 h, it was not possible to reliably measure the reaction rate, therefore, a loading of 0.1 mol % was used (FIG. 3b). A comparison with the in situ protocol is shown after 1 hour. Given that both reactions were 30% complete at that time, the apparent (turnover numbers) TONs suggest, assuming the same active catalyst is generated when employing the in situ protocol, that only ~0.1 mol % of active catalyst is actually formed, even though 4 mol % of the precursors are used. It should be pointed out that, in the prior art Pd$_2$(dba)$_3$/IIa in situ protocol, the catalysis was weighed in a glove box, taking great care to avoid contact with air and water. Using the compounds of formula I of the present invention, the catalyst (or precatalyst) could be weighed in the open with no special precautions to avoid contact with air. The advantages in reaction time and yield when the compounds of formula I are used in the metal-catalyzed cross-coupling reaction are clearly seen in the graphs shown in FIG. 3. Further, reliable and repeatable results could not be obtained using the prior art catalyst owing, potentially, to the uncertainty in the composition of the prior art in situ generated catalyst. The methods of the present invention, by employing a stable catalyst precursor having a well-defined structure, provides a significant improvement in the performance of NHC—Pd(0) catalyst systems.

Example 6

Optimization of Suzuki Conditions for Boronic Acids

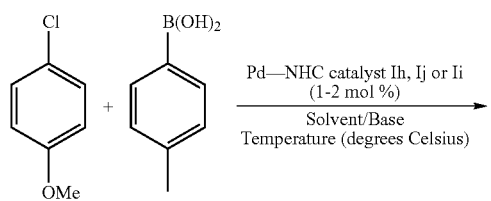

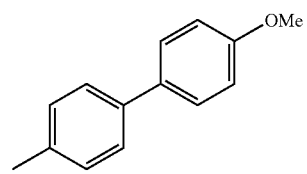

Complexes Ih, Ij or Ii was subjected to a variety of Suzuki reaction conditions (Table 2). It was found that all complexes functioned as excellent catalysts at 80° C. In comparison to complexes Ij and Ii, it was found that complex Ih was advantageous as it was possible to conduct reactions in both dioxane and i-PrOH at room temperature with a judicious choice of base (Table 2, entries, 10 and 12).

Example 7

Optimization of Suzuki Conditions for Potassium Trifluoroborates

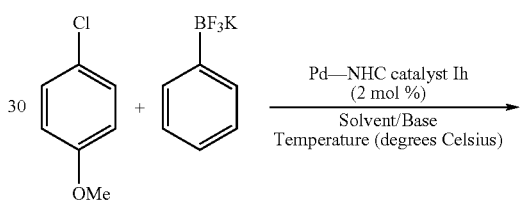

Expansion of the protocol in Example 6 to potassium trifloroboroates was accomplished by simply changing the solvent to methanol (Table 3, entries 2, 5, 6-8).

Example 8

Suzuki Cross-coupling Reactions Substrate Scope

There are 4 different protocols for this reaction dependent on the coupling partners. Robust functionality can be coupled at room temperature in isopropyl alcohol (IPA) using KOt-Bu as base, while base-sensitive groups may be coupled utilizing K$_2$CO$_3$ at 60° C. For relatively hindered substrates sensitive to KOt-Bu and where K$_2$CO$_3$ is ineffective, KOH may be used at room temperature. Optimal to the success is ensuring that the precatalyst is activated. When utilizing KOt-Bu, a change in reaction solution color, nor mally to orange or red, is observed. When utilizing $K_2CO_3$ or KOH, in the absence of strongly colored materials the reaction is generally complete when the solution is grey in color and contains noticeable precipitate.

The employment of a variety of reaction conditions allowed a large array of hindered biaryls and drug-like heteroaromatics to be easily synthesized using Suzuki cross-coupling reaction conditions (Table 4). A notable example is the synthesis of 19 (Table 4), which when used in combination with triethylphosphine has been demonstrated to form a highly effective asymmetric Morita-Baylis-Hillman (MBA) protocol [McDougal, N. T.; Schaus, S. E. J. Am. Chem. Soc. (2003) 125, 12094-12095]. Methods A, B, C and D are described in detail below. Use of IPA/t-BuOK (Method A) allowed for rapid cross-coupling at room temperature whereas more sensitive coupling partners were effectively coupled utilizing mild $K_2CO_3$ in dioxane (Method B) or methanol in the case of potassium trifluoroborates (Method C).

(i) Procedure for Method A.

In air, a vial was charged with potassium tert-butoxide (154 mg, 1.30 mmol) and complex Ih (6.8 mg, 0.01 mmol) and the vial was sealed and purged with argon (3×). Technical grade isopropanol (1.0 mL) was added and the contents were stirred at room temperature until a colour change from yellow to red/brown was observed (~10 min). Under a cone of argon, the boronic acid (1.20 mmol) was added, the vial was resealed with a septum and the organohalide (1.00 mmol) injected via microliter syringe. Alternatively, if the boronic acid was soluble in isopropanol, it was added as a solution (1.0 mL). The solution was stirred at room temperature for the indicated period of time. The reaction was then diluted with diethyl ether (2 mL) and transferred to a round bottom flask. The reaction vial was rinsed with additional diethyl ether (2 mL) and combined with the previous dilution. Each reaction was performed in duplicate and the contents were combined, concentrated onto silica gel and purified by flash chromatography.

(ii) Procedure for Method B.

In air, a vial was charged with complex Ih (6.8 mg, 0.01 mmol), potassium carbonate (207 mg, 1.50 mmol), the boronic acid (0.6 mmol) and the organohalide (0.5 mmol). The vial was sealed with a septum and purged with argon (3×). Dioxane (2.0 mL) was added and the contents were stirred at 60° C. for the specified period of time. The reaction was then diluted with diethyl ether (2 mL) and transferred to a round bottom flask. The reaction vial was rinsed with additional diethyl ether (2 mL) and combined with the previous dilution. Each reaction was performed in duplicate and the contents were combined, concentrated onto silica gel and purified by flash chromatography.

(iii) Procedure for Method C.

In air, a vial was charged with complex Ih (6.8 mg, 0.01 mmol), potassium carbonate (207 mg, 1.50 mmol), the potassium trifluoroborate (0.55 mmol) and the organohalide (0.5 mmol). The vial was sealed with a septum and purged with argon (3×). Technical grade methanol (2.0 mL) was added and the contents stirred at 60° C. for the specified period of time. The reaction was then diluted with diethyl ether (2 mL) and transferred to a round bottom flask. The reaction vial was rinsed with additional diethyl ether (2 mL) and combined with the previous dilution. Each reaction was performed in duplicate and the contents were combined, concentrated onto silica gel and purified by flash chromatography.

(iv) Procedure for Method D.

Method B was followed however in the place of solid potassium carbonate, solid KOH (84 mg, 1.50 mmol) was utilized. Additionally, the reaction was carried out at room temperature instead of 60° C.

Example 9

Evaluation of Complex Ih in the Negishi Reaction

A comprehensive evaluation of complex Ih in the Negishi cross-coupling reaction was performed. The results presented in Table 5 demonstrate that complex Ih was able to catalyze the cross-coupling of organo-chlorides, bromides and iodides, aryl triflates and alkyl tosylates and mesylates in all possible pairings of potential cross-coupling substrates, including all possible hybridization states of the atoms specifically involved in the coupling, in high yield at room temperature (Table 5, entries 1-3, 6-8, 12-14 and 17-19).

There were 4 main protocols for this reaction dependant on organohalide and carbon hybridization present in the coupling partners. Whilst most reactions are carried out at room temperature, sterically encumbered partners were optimally warmed to 60-70° C. to ensure efficient cross-coupling. Furthermore, the addition of 2 equivalents (based on organozinc) of LiBr or LiCl (available from Aldrich as 1M anhydrous solutions in THF or DMI) is important to effect cross-coupling in some reaction types (see Protocols below). Efficient catalyst formation and reaction is normally indicated by a slow color change from pale yellow to a deep brown-colored solution when employing zinc made by the Hou protocol in DMI (*Org. Lett.* 2003, 5, 423). If this change is rapid, (1-2 seconds) this is indicative of a failed reaction and is normally the result of ineffective catalyst activation, which could be due to the steric and/or electronic properties of the organozinc reagent. Use of organozincs formed by Rieke zinc does not show the same color change. Additionally, the use of n-BuLi for formation of aryl zincs should be avoided as the generated butyl halide is a capable coupling partner for complex Ih due to its high reactivity.

Cross-Coupling Procedures: All cross-coupling reactions were run with a final solvent volume of 2.4 mL.

Solvent Ratios

Alkyl bromides: DMI/NMP: THF, 1:2

Alkyl chlorides, iodides, tosylates and mesylates: DMI/NMP: THF, 3:1

Aryl bromides: DMI/NMP: THF, 1:2

Aryl chlorides, triflates: DMI/NMP:THF, 3:1

($sp^3$X-$sp^3$ZnX): A vial was charged with Ih (3.4 mg, 1 mol %), LiBr (139.0 mg, 1.6 mmol, transferred under a filter cone flowing with inert gas) and a stirbar, after which it was sealed with a septum and purged under an inert atmosphere. THF (X mL) and DMI (X mL) or NMP (X mL) were then added and the suspension stirred until the solids dissolved after which the organozinc (0.8 mL, 1.0 M in DMI or NMP, 0.8 mmol) and the organohalide or pseudo halide (0.5 mmol) were added. The septum was replaced with a Teflon®-lined screw cap under an inert atmosphere (e.g. under a cone of argon, not necessarily in a glove box) and the reaction stirred for 2 h. After this time, the mixture was diluted with ether (15 mL) and washed successively with 1 M $Na_3EDTA$ solution (prepared from EDTA and 3 equiv of NaOH), water and brine.

After drying (anhydrous MgSO$_4$) the solution was filtered, the solvent removed in vacuo, and the residue purified by flash chromatography.

(sp$^3$X-sp$^2$ZnX): A vial was charged with Ih (3.4 mg, 1 mol %) and under an inert atmosphere ZnCl$_2$ (107 mg, 0.8 mmol, transferred under a filter cone flowing with inert gas) and a stirbar were added. The vial was then sealed with a septum and purged under an inert atmosphere. THF (0.8 mL) was added followed by the requisite Grignard reagent (0.8 mL, 1.0 M in THF, 0.8 mmol) and stirring continued for 15 minutes at which time a white precipitate formed. Under an inert atmosphere, LiBr (139.0 mg, 1.6 mmol), NMP (0.8 mL) or DMI (0.8 mL) and the organohalide or psuedo halide (0.5 mmol) were added. The septum was replaced with a Teflon®-lined screw cap under an inert atmosphere and the reaction stirred for 2 h. After this time, the mixture was diluted with ether (15 mL) and washed successively with 1 M Na$_3$EDTA solution (prepared from EDTA and 3 equiv of NaOH), water and brine. After drying (anhydrous MgSO$_4$) the solution was filtered, the solvent removed in vacuo, and the residue purified by flash chromatography.

(sp$^2$X-sp$^3$ZnX): A vial was charged with Ih (3.4 mg, 1 mol %), LiBr (139.0 mg, 1.6 mmol, transferred under a filter cone flowing with inert gas) and a stirbar after which it was sealed with a septum and purged under an inert atmosphere. THF (X mL) and DMI (X mL) or NMP (X mL) were then added and the suspension stirred until the solids dissolved after which the organozinc (0.8 mL, 1.0 M in DMI or NMP, 0.8 mmol) and the organohalide or psuedo halide (0.5 mmol) were added. The septum was replaced with a Teflon®-lined screw cap under an inert atmosphere and the reaction stirred for 2 h. After this time, the mixture was diluted with ether (15 mL) and washed successively with 1 M Na$_3$EDTA solution (prepared from EDTA and 3 equiv of NaOH), water and brine. After drying (anhydrous MgSO$_4$), the solution was filtered, the solvent removed in vacuo, and the residue purified by flash chromatography.

(sp$^2$X-sp$^2$ZnX): In air, a vial was charged with 1 h (3.4 mg, 1 mol %) and ZnCl$_2$ (0.8 mmol, transferred under a filter cone flowing with inert gas) and a stirbar were added. The vial was then sealed with a septum and purged under an inert atmosphere. THF (X mL) was then added followed by the requisite Grignard reagent (0.8 mL, 1.0 M in THF, 0.8 mmol) and stirring continued for 15 minutes at which time a white precipitate formed. NMP (X mL) was then added followed by the organohalide or pseudo halide (0.5 mmol) and the septum was replaced with a Teflon®-lined screw cap under an inert atmosphere and the reaction stirred for 2 h. After this time, the reaction mixture was diluted with ether (15 mL) and washed successively with 1 M Na$_3$EDTA solution (prepared from EDTA and 3 equiv of NaOH), water and brine. After drying (anhydrous MgSO$_4$) the solution was filtered, the solvent removed in vacuo, and the residue purified by flash chromatography.

Example 10

Negishi Cross-coupling Reactions Substrate Scope

As seen in Table 6, functionalization of the reactants did not diminish the generality of the protocols described in Example 9, with sp$^3$(RX)-sp$^3$(RZnX), sp$^3$-sp$^2$, sp$^2$-sp$^3$ and sp$^2$-sp$^2$ cross-coupling reactions easily accomplished with 1 mol % complex Ih. Coupling of a range of alkyl bromides, chlorides and tosylates was achieved at room temperature (Table 6, compounds 21-26). Remarkably, by careful choice of reaction conditions it was possible to selectively couple a bromide in the presence of a chloride (Table 6, compound 21). An array of functionality was tolerated including esters, nitriles, amides and acetals (Table 6, 21-26). Noteworthy examples are the coupling of (S)-citronellyl bromide in high yield (Table 6, compound 27) and the stability of the TMS group in the reaction conditions (Table 6, compounds 25, 28 and 29). The coupling of alkyl zinc reagents with aryl halides or aryl triflates occurred in high yield with no transmetalation to the aryl zinc observed (Table 6, compounds 31-34). Aryl halides, as expected, proved to be excellent coupling partners. Accordingly, the facile synthesis of a range of drug-like heteroaromatics and sterically congested biaryls was accomplished in high yield (Table 6, compounds 35-41). A significant entry is the coupling of o-chlorotoluene and 2,4,6-triisopropylphenylzinc chloride at 60° C. (Table 6, compound 35). N-Boc protected indole, pyridine, and multiple heteroatom containing heterocycles were well tolerated (Table 6, compounds 31, 32, 34, 37, 39-41). Finally, the cross-coupling of a chiral zinc reagent with an acyl chloride (Table 6, compound 33) proceeded without concomitant decarbonylation, demonstrating the mildness of this protocol.

Example 11

Heck Cross-coupling Reaction

A vial was charged with complex Ih (17.0 mg, 0.025 mmol, 5 mol %) as defined in Example 1, Cs$_2$CO$_3$ (326 mg, 1.0 mmol) and a stir bar. The air was replaced with an inert gas (Ar) and dry DMA was introduced, followed by bromobenzene (53 μL, 78.5 mg, 0.5 mmol), tert-butyl acrylate (117 μL, 103 mg, 0.8 mmol) and n-undecane (GC internal standard, 50 μL). The reaction was stirred at 120° C. for 18 hours, then cooled to room temperature, diluted with hexane and analyzed by GC/MS after passing through a short pad of silica gel. Quantitative conversion to (E)-tert-butyl cinnamate was observed by GC/MS. GC retention time and EI fragmentation pattern were identical to commercially available material (Aldrich).

Example 12

Buchwald-Hartwig Coupling Reaction

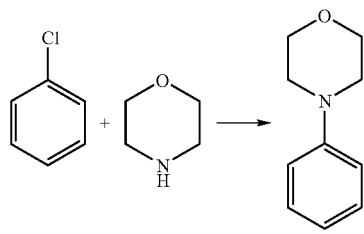

In air, potassium tert-butoxide (127 mg, 1.10 mmol) and complex Ih (6.8 mg, 0.01 mmol, 1.0 mol %) as defined in Example 1 were weighed into a vial with a stir bar and the vial was capped with a septum. The atmosphere was replaced with inert gas (Ar) and 1 mL of dry DME added and stirred until all the solids had dissolved. Chlorobenzene (102 µL, 112.56 mg, 1.0 mmol) and morpholine (96 µL, 96 mg, 1.10 mmol) were then added in quick succession with rapid stirring. The septum was then replaced with a Teflon® lined cap under inert gas (Ar) and the vial heated at 50° C. for 1 hour. After this time the reaction mixture was cooled and partitioned between water and ether, the organic phase was dried (anhydrous MgSO$_4$), filtered, and the solvent removed. The resultant residue was purified by flash chromatography eluting with 9:1 pentane:ether. N-Phenylmorpholine was obtained as a white solid 155 mg, 95% yield.

Example 13

Buchwald-Hartwig Coupling Reactions Substrate Scope

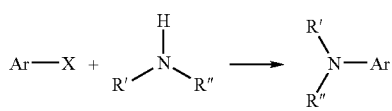

A study of the Buchwald-Hartwig coupling reaction substrate scope was performed and the results are shown in Table 7. The general experimental conditions were as follows:

A vial was charged with Ih (14 mg, ~2 mol %), KOt-Bu (135.0 mg, 1.2 mmol corrected for purity) and a stirbar were added after which it was sealed with a septum and purged with an inert atmosphere. The amine (1.1 mmol) and organohalide (1.0 mmol) were added and stirred rapidly for 1-2 min. When using 2,6-diisopropylaniline the reaction turns orange immediately; stirring should continue until the solution becomes dark orange to red (note: a green to dark green solution indicates a failure to form sufficient active catalyst). After this time, DME (1 mL) was added and the septum was replaced with a Teflon®-lined screw cap under an inert atmosphere and the reaction stirred at RT or 50° C. until complete. After this time, the mixture was diluted with TBME (15 mL) and washed with water. After drying (anhydrous Na$_2$SO$_4$, the use of MgSO$_4$ can be problematic), the solution was filtered, the solvent removed in vacuo, and the residue purified rapidly by flash chromatography and stored under an inert atmosphere. Pre-absorption of the crude amine product onto silica should be avoided as this practice has been found to lead to poor recovery.

Example 14

Kumada Reaction

Effective coupling partners are aryl chlorides and bromides. Simple couplings can be done at room temperature without the addition of LiCl; if this proves unproductive, heating at 60 or 70° C. normally facilitates the cross-coupling. If these conditions fail for challenging partners, 2 or 3 equivalents (based on organomagnesium reagent) of anhydrous LiCl may be added and the reaction temperature varied from RT to 70° C.

A vial was charged with Ih (7 mg, 2 mol %) and LiCl (67.0 mg, 1.6 mmol) as necessary followed by a stirbar under an inert atmosphere. The vial was then sealed with a septum and purged under an inert atmosphere after which DME (0.8 mL) was added and the suspension was stirred until 1 h had dissolved. After this time, the organohalide (0.5 mmol) and the organomagnesium (0.8 mL, 1.0 M in THF or ether, 0.8 mmol) were added (active catalyst is indicated by the reaction solution turning orange). The septum was replaced with a Teflon®-lined screw cap under an inert atmosphere and the reaction stirred at RT or warmed to 60 or 70° C. until complete. After this time, the mixture was diluted with a suitable organic solvent (15 mL) and washed successively with 1 M Na$_3$EDTA solution (prepared from EDTA and 3 equiv of NaOH), water and brine. After drying (anhydrous MgSO$_4$) the solution was filtered, the solvent removed in vacuo, and the residue purified by flash chromatography. A summary of the substrate scope that was explored is presented in Table 8.

Example 15

Enolate Arylation

General procedure: In air a vial was charge with Ih or Ik (1 mol %, 6 mg), sodium tert-butoxide (1.5 mmol, 1.44 mg) the vial was then purged with Ar. After which toluene (1 mL), ketone (1.1 mmol) and the aryl chloride (1.0 mmol) were added in turn and sealed with a screw cap. The vial was then placed in an oil bath at 60° C. and the mixture stirred on a stirring plate. When reaction reached completion, or no further conversion could be observed by TLC, the vial was allowed to cool to room temperature. Water was added to the reaction mixture; the organic layer was extracted with diethyl ether and dried over magnesium sulfate. The solvent was then evaporated in vacuo and the product purified by column chromatography.

Representative Example

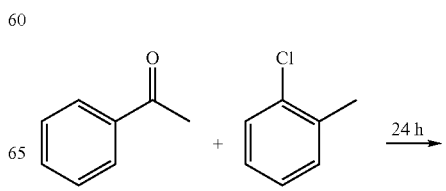

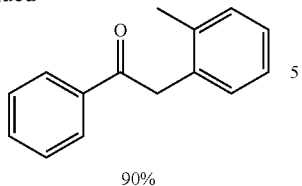

90%

Example 16

Sonogashira Reaction (i) Primary Alkyl Bromides

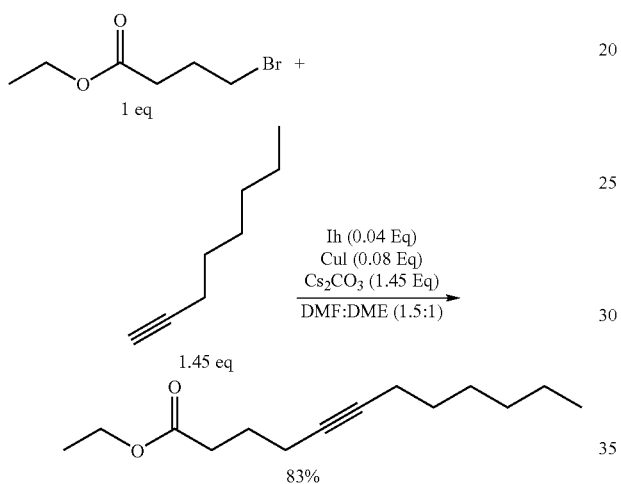

83%

A powder of 1 h (0.8500 g)/CuI (0.4750 g) was prepared. In air, the Ih/CuI powder (21.2 mg) and Cs$_2$CO$_3$ (0.7 mmol, 228.0 mg) were added to a vial equipped with a magnetic bar, and sealed with a Teflon®-lined screw cap and fitted with a septum. The vial was purged with Argon, and DMF (1.2 mL) followed by DME (0.8 mL) were added. The contents were allowed to stir at room temperature for 30 min. The alkyl bromide (0.5 mmol, 67 μL), followed by the octyne (0.73 mmol, 110 μL) were added. The vial was then placed in an oil bath at 60° C. for 18 h. An aqueous workup was performed, the organic layer extracted with pentane and dried over MgSO$_4$. The solvent was removed using a rotary evaporator and the product was purified using flash chromatography with 2% ether/pentane eluent, yielding 92.6 mg of the product.

(ii) Secondary Alkyl Bromides

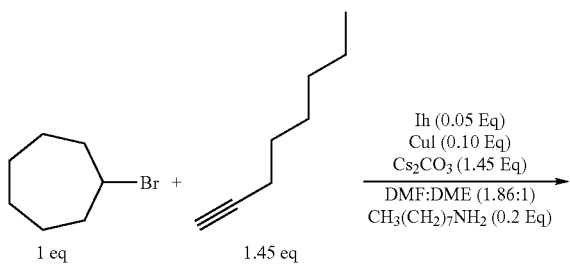

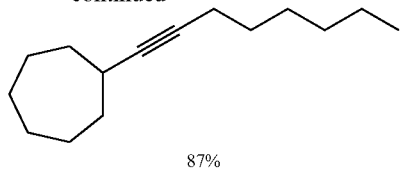

87%

A powder of 1 h (0.8500 g)/CuI (0.4750 g) was prepared. In air, the Ih/CuI powder (26.5 mg) and Cs$_2$CO$_3$ (0.7 mmol, 228.0 mg) were added to a vial equipped with a magnetic bar, and sealed with a Teflon®-lined screw cap and fitted with a septum. The vial was purged with Argon and DMF (1.3 mL) followed by DME (0.7 mL) were added. The contents were allowed to stir at room temperature for 30 min. The octylamine (20 mol %, 16.5 μL) was added at the end of the stirring time followed by the alkyl bromide (0.5 mmol, 67 μL), followed by the octyne (0.73 mmol, 110 μL). The vial was then placed in an oil bath at 60° C. for 18 h. An aqueous workup was performed, the organic layer extracted with pentane and dried over MgSO$_4$. The solvent was removed using a rotary evaporator and purified using flash chromatography with hexane eluent. 90.3 mg of the product, determined by NMR, was isolated.

Example 17

Bis Pinicol Borane

In air, a vial was charged with Ih (10.2 mg, 0.015 mmol, 3 mol %), bis(pinacolato)diboron (0.1397 g, 0.55 mmol) and KOAc (0.147 g, 1.5 mmol). The vial was sealed and purged with argon. Bromobenzene (52 μL, 0.5 mmol) and 3 mL of DMSO were then added. The resulting mixture was then stirred at 90° C. until the reaction was complete. The product was extracted into ether, separated and dried over MgSO$_4$. The product was purified by column chromatography. Results for various substrate scope and reaction conditions are presented in Table 9.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

CATALYTIC ACTIVITY OF THE NHC—Pd COMPLEXES Ih, Ij AND Ii IN ALKYL-ALKYL CROSS-COUPLING REACTIONS

| entry | M | yield of n-heptylbenzene[a,b] |
|---|---|---|
| 1 | ZnBr[c] | 100% (Ih), 34% (Ij), 8.0% (Ii) |
| 2 | BBu$_2$[d] | 100% (Ih), 31% (Ij), 6.5% (Ii) |
| 3 | MgBr[e] | 100% (Ih) |

[a]GC yield (internal standard-undecane) after 24 hours at room temperature; all reactions in duplicate.
[b]Control experiments with no catalyst showed no conversion in all cases.
[c]n-Butylzinc bromide (1.3 equiv), THF-NMP = 2:1.
[d]tri-n-butylborane (1.2 equiv), t-BuOK (1.3 equiv), i-PrOH.
[e]n-Butyl magnesium bromide (1.5 eq), 1-chloro-3-phenylpropane used instead of 1-bromo-3-phenylpropane, THF:DMI = 2:1, RT, 45 min.

TABLE 2

OPTIMIZATION OF SUZUKI CONDITIONS FOR BORONIC ACIDS

| entry[a] | catalyst (mol %) | solvent | base (Equiv) | temp. (° C.) | yield (%)[b,c] |
|---|---|---|---|---|---|
| 1 | Ii (2) | Dioxane | Cs$_2$CO$_3$ (2) | 80 | 74 |
| 2 | Ij (2) | Dioxane | Cs$_2$CO$_3$ (2) | 80 | 95 |
| 3 | Ij (2) | DME | Cs$_2$CO$_3$ (2) | 80 | 54 |
| 4 | Ih (2) | Dioxane | K$_3$PO$_4$ (2) | 80 | 48 |
| 5 | Ih (2) | Dioxane | Cs$_2$CO$_3$ (2) | 80 | 92 |
| 6 | Ih (2) | DME | Cs$_2$CO$_3$ (2) | 80 | 77 |
| 7 | Ih (2) | Dioxane | K$_2$CO$_3$ (2) | 80 | 80 |
| 8 | Ih (2) | Dioxane | K$_2$CO$_3$ (3) | 80 | 95 |
| 9 | Ih (2) | Dioxane | K$_2$CO$_3$ (3) | 60 | 97 |
| 10 | Ih (2) | Dioxane | K$_2$CO$_3$ (3) | rt | 86 |
| 11 | Ih (1) | Dioxane | K$_2$CO$_3$ (3) | 80 | 74 |
| 12 | Ih (1) | i-PrOH | t-BuOK | rt | 97 |

[a]GC yield (internal standard-undecane) after 2 hours at room temperature; all reactions in duplicate.
[b]Control experiments with no catalyst showed no conversion.

TABLE 3

OPTIMIZATION OF SUZUKI CONDITIONS FOR POTASSIUM TRIFLUOROBORATES

| entry | solvent | base (Equiv) | temp. (° C.) | yield (%)[a,b] |
|---|---|---|---|---|
| 1 | Dioxane | K$_2$CO$_3$ (3) | 60 | 0 |
| 2 | MeOH | K$_2$CO$_3$ (3) | 60 | 90 |
| 3 | EtOH | K$_2$CO$_3$ (3) | 60 | 30 |
| 4 | i-PrOH | K$_2$CO$_3$ (3) | 60 | 27 |
| 5 | MeOH | K$_2$CO$_3$ (3) | rt | 86 |
| 6 | MeOH | CsF | 60 | 0 |
| 7 | MeOH | KOH | 60 | 91 |
| 8 | MeOH | K$_3$PO$_4$ | 60 | 84 |

[a]GC yield (internal standard-undecane) after 24 hours at room temperature; all reactions in duplicate.
[b]Control experiments with no catalyst showed no conversion.

TABLE 4

OPTIMIZATION OF SUZUKI CONDITIONS FOR POTASSIUM TRIFLUOROBORATES USING COMPLEX Ih AS THE CATALYST

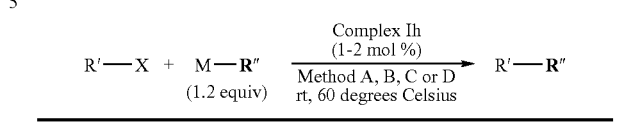

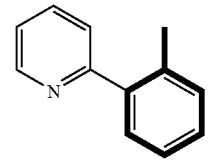

(8, 93%, 2 h, Method A)[a]
(X = Cl, M = B(OH)$_2$)

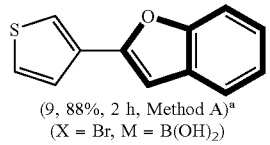

(9, 88%, 2 h, Method A)[a]
(X = Br, M = B(OH)$_2$)

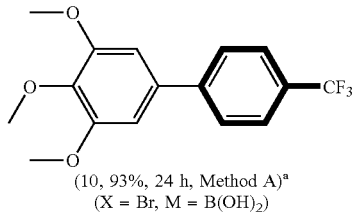

(10, 93%, 24 h, Method A)[a]
(X = Br, M = B(OH)$_2$)

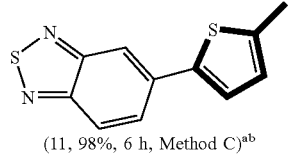

(11, 98%, 6 h, Method C)[a,b]
(X = Br, M = BF$_3$K)

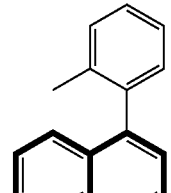

(12, 85%, 2 h, Method A)[a]
(X = Cl, M = B(OH)$_2$)

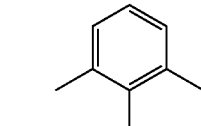

(13, 85%, 2 h, Method A)[a]
(X = Cl, M = B(OH)$_2$)

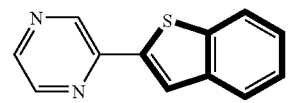

TABLE 4-continued

OPTIMIZATION OF SUZUKI CONDITIONS FOR POTASSIUM TRIFLUOROBORATES USING COMPLEX Ih AS THE CATALYST

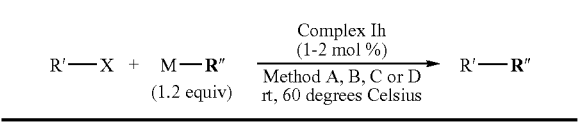

$$R'\text{---}X + M\text{---}R'' \xrightarrow[\text{rt, 60 degrees Celsius}]{\text{Complex Ih (1-2 mol \%)} \atop \text{Method A, B, C or D}} R'\text{---}R''$$
(1.2 equiv)

(14, 96%, 2 h, Method B)[a]
(X = Cl, M = B(OH)$_2$)

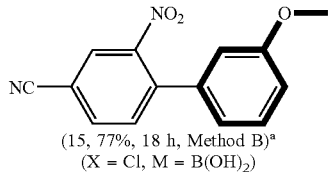

(15, 77%, 18 h, Method B)[a]
(X = Cl, M = B(OH)$_2$)

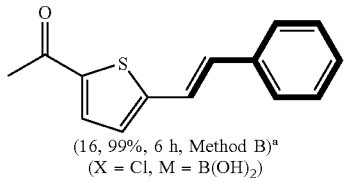

(16, 99%, 6 h, Method B)[a]
(X = Cl, M = B(OH)$_2$)

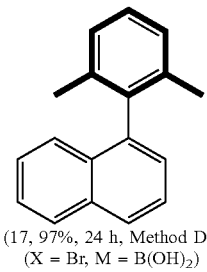

(17, 97%, 24 h, Method D)[a]
(X = Br, M = B(OH)$_2$)

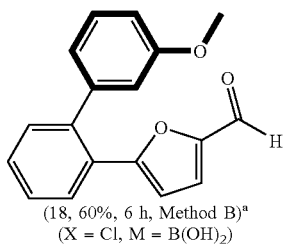

(18, 60%, 6 h, Method B)[a]
(X = Cl, M = B(OH)$_2$)

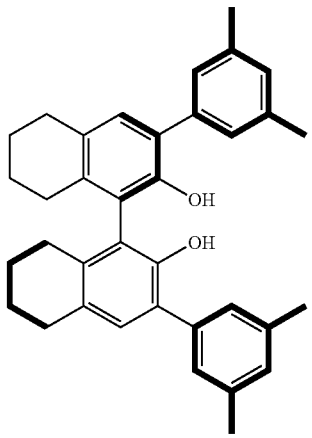

(19, 93%, 16 h, Method B)[a,c]
(X = Br, M = B(OH)$_2$)

TABLE 4-continued

OPTIMIZATION OF SUZUKI CONDITIONS FOR POTASSIUM TRIFLUOROBORATES USING COMPLEX Ih AS THE CATALYST

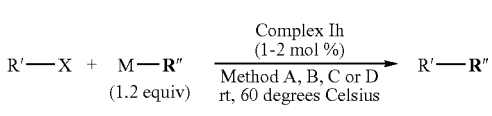

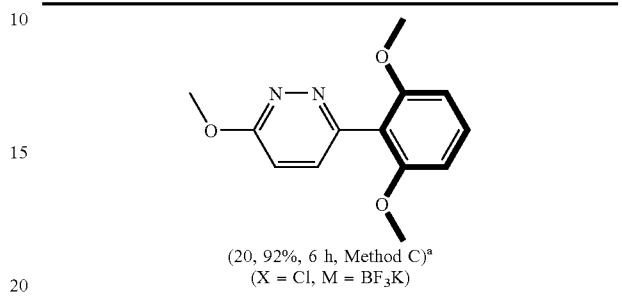

(20, 92%, 6 h, Method C)[a]
(X = Cl, M = BF$_3$K)

[a]All reactions were performed using standard laboratory technique, i.e. no glove-box was employed: Method A: Ih (1 mol %), K$^t$OBu (1.3 equiv.), reagent grade isopropanol, room temperature. Method B: Ih (2 mol %), dioxane, 60° C. Method C: Ih (2 mol %), K$_2$CO$_3$ (3.0 equiv.), methanol, 60° C. Method D: Ih (2 mol %), KOH$_s$ (3.0 equiv.), dioxane, rt.
[b]Yielded 70% after 12 h at rt.
[c]Using Ih (4 mol %) K$_2$CO$_3$ (6.0 equiv) and RB(OH)$_2$ (2.4 equiv).

TABLE 5

EVALUATION OF COMPLEX Ih IN THE NEGISHI REACTION

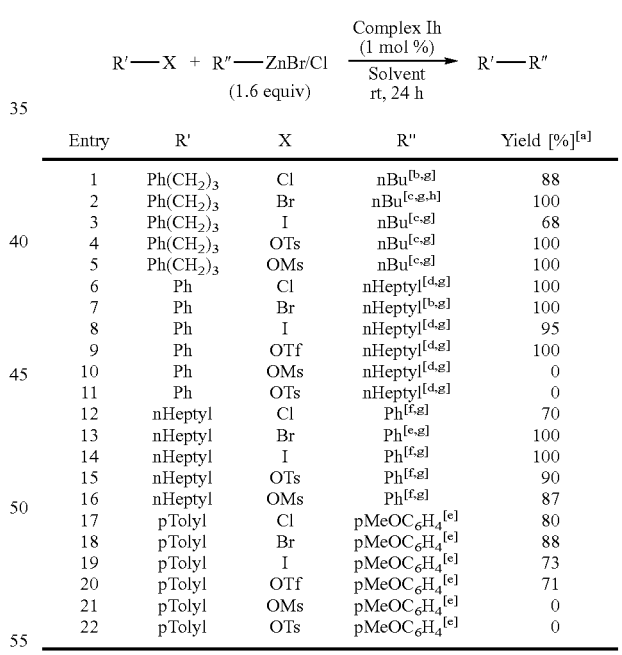

$$R'\text{---}X + R''\text{---}ZnBr/Cl \xrightarrow[\text{rt, 24 h}]{\text{Complex Ih (1 mol \%)} \atop \text{Solvent}} R'\text{---}R''$$
(1.6 equiv)

| Entry | R' | X | R'' | Yield [%][a] |
|---|---|---|---|---|
| 1 | Ph(CH$_2$)$_3$ | Cl | nBu[b,g] | 88 |
| 2 | Ph(CH$_2$)$_3$ | Br | nBu[c,g,h] | 100 |
| 3 | Ph(CH$_2$)$_3$ | I | nBu[c,g] | 68 |
| 4 | Ph(CH$_2$)$_3$ | OTs | nBu[c,g] | 100 |
| 5 | Ph(CH$_2$)$_3$ | OMs | nBu[c,g] | 100 |
| 6 | Ph | Cl | nHeptyl[d,g] | 100 |
| 7 | Ph | Br | nHeptyl[b,g] | 100 |
| 8 | Ph | I | nHeptyl[d,g] | 95 |
| 9 | Ph | OTf | nHeptyl[d,g] | 100 |
| 10 | Ph | OMs | nHeptyl[d,g] | 0 |
| 11 | Ph | OTs | nHeptyl[d,g] | 0 |
| 12 | nHeptyl | Cl | Ph[f,g] | 70 |
| 13 | nHeptyl | Br | Ph[e,g] | 100 |
| 14 | nHeptyl | I | Ph[f,g] | 100 |
| 15 | nHeptyl | OTs | Ph[f,g] | 90 |
| 16 | nHeptyl | OMs | Ph[f,g] | 87 |
| 17 | pTolyl | Cl | pMeOC$_6$H$_4$[e] | 80 |
| 18 | pTolyl | Br | pMeOC$_6$H$_4$[e] | 88 |
| 19 | pTolyl | I | pMeOC$_6$H$_4$[e] | 73 |
| 20 | pTolyl | OTf | pMeOC$_6$H$_4$[e] | 71 |
| 21 | pTolyl | OMs | pMeOC$_6$H$_4$[e] | 0 |
| 22 | pTolyl | OTs | pMeOC$_6$H$_4$[e] | 0 |

[a]GC yield against calibrated internal standard (undecane) performed in duplicate.
[b]THF:DMI, 2:1.
[c]THF:DMI, 1:3.
[d]THF:DMI, 1:2,
[e]THF:NMP, 2:1.
[f]THF:NMP, 1:2.
[g]LiBr or LiCl (2 equiv relative to the organozinc reagent) was added.
[h]Yield 63% after 24 hours with a catalyst loading of 0.1 mol %

[a] yield against calibrated internal standard (undecane) performed in duplicate. [b] THF:DMI, 2:1. [c] THF:DMI, 1:3. [d] THF:DMI, 1:2, [e] THF:NMP, 2:1. [f] THF:NMP, 1:2. [g] LiBr or LiCl (2 equiv relative to the organozinc reagent) was added. [h] Yield 63% after 24 hours with a catalyst loading of 0.1 mol %

TABLE 6

EVALUATION OF COMPLEX Ih IN THE NEGISHI REACTION: SUBSTRATE SCOPE

R′—X + R″—ZnBr/Cl (1.6 equiv) → R′—R″
Complex Ih (1 mol %)
THF/NMP or THF/DMI
rt to 60 degrees Celsius, 2 h sp³-sp³

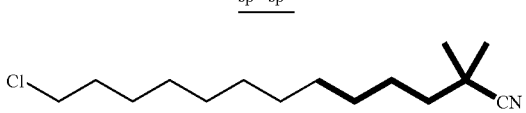

21, 81%, X = Br, rt

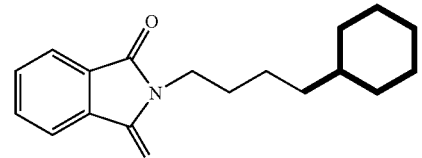

22, 80%, X = Br, rt

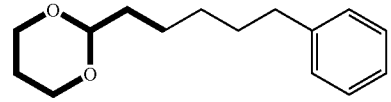

23, 86%, X = Br, rt

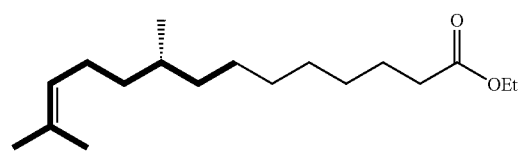

24, 87%, X = Br, rt

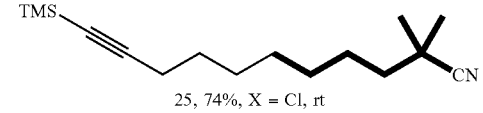

25, 74%, X = Cl, rt

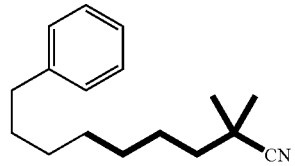

26, 70%, X = OTs, rt sp³-sp²

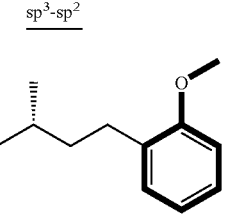

27, 87%, X = Br, rt

TABLE 6-continued

EVALUATION OF COMPLEX Ih IN THE NEGISHI REACTION: SUBSTRATE SCOPE

R′—X + R″—ZnBr/Cl (1.6 equiv) → R′—R″
Complex Ih (1 mol %)
THF/NMP or THF/DMI
rt to 60 degrees Celsius, 2 h

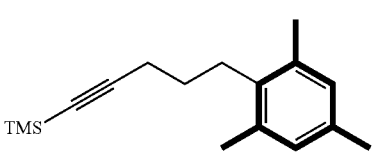

28, 89%, X = Cl, rt 29, 92%, X = Cl, rt 30, 91%, X = OTs, rt sp²-sp³

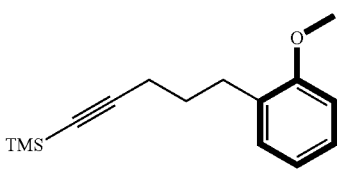

31, 81%, X = OTf, rt 32, 98%, X = Cl, rt 33, 87%, X = Cl, rt

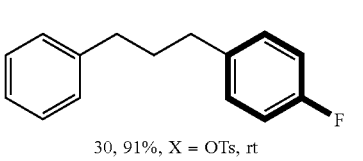

34, 83%, X = Br, rt

TABLE 6-continued

EVALUATION OF COMPLEX Ih IN THE NEGISHI REACTION: SUBSTRATE SCOPE

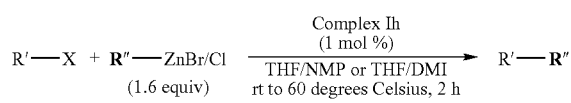

sp²-sp²

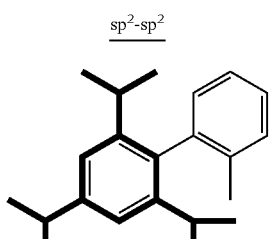

35, 90%, X = Cl, 60 degrees Celsius

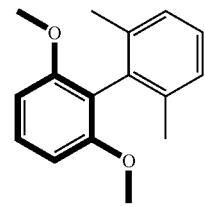

36, 89%, X = Cl, 60 degrees Celsius

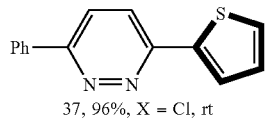

37, 96%, X = Cl, rt

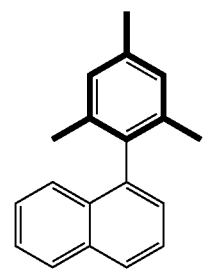

38, 96%, X = Br, rt

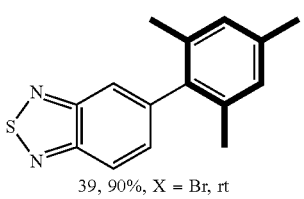

39, 90%, X = Br, rt

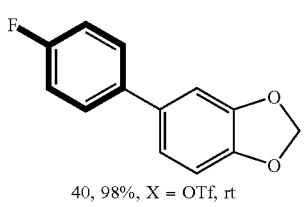

40, 98%, X = OTf, rt

TABLE 6-continued

EVALUATION OF COMPLEX Ih IN THE NEGISHI REACTION: SUBSTRATE SCOPE

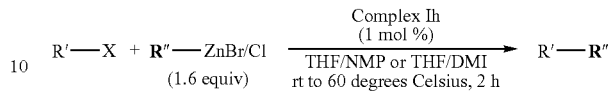

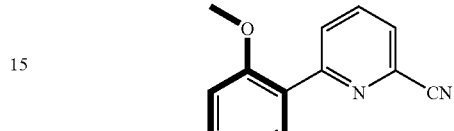

41, 90%, X = Cl, rt

TABLE 7

EVALUATION OF COMPLEX Ih IN THE BUCHWALD-HARTWIG REACTION: SUBSTRATE SCOPE

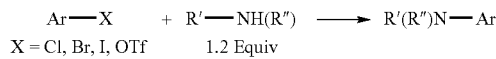

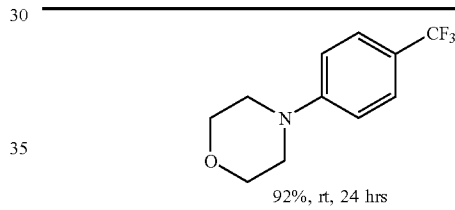

92%, rt, 24 hrs
Cl

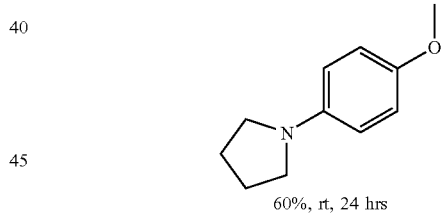

60%, rt, 24 hrs
Cl

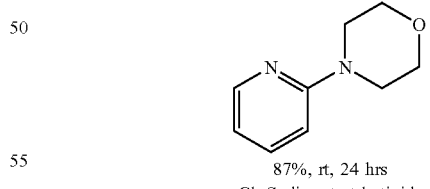

87%, rt, 24 hrs
Cl, Sodium tert-butixide

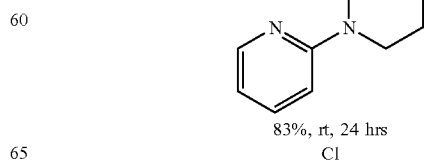

83%, rt, 24 hrs
Cl

TABLE 7-continued

EVALUATION OF COMPLEX Ih IN THE BUCHWALD-HARTWIG REACTION: SUBSTRATE SCOPE

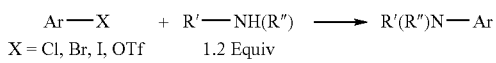

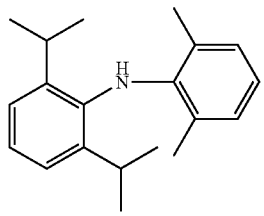

90%, rt, 24 hrs
Cl, Sodium-tert-butoxide

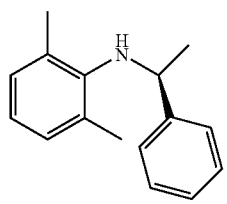

78%, rt, 24 hrs
Cl, Sodium-tert-butoxide

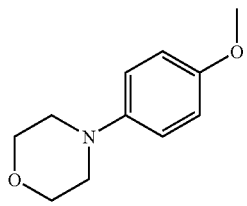

87%, rt, 24 hrs
Cl

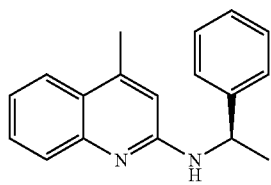

88%, 50° C., 24 hrs
Cl, Sodium tert-butoxide

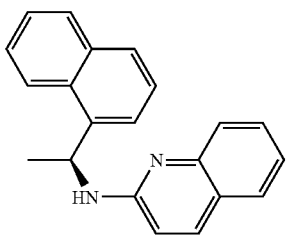

96%, 50° C., 48 hrs
Cl, Sodium tert-butoxide

TABLE 7-continued

EVALUATION OF COMPLEX Ih IN THE BUCHWALD-HARTWIG REACTION: SUBSTRATE SCOPE

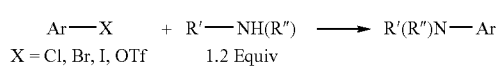

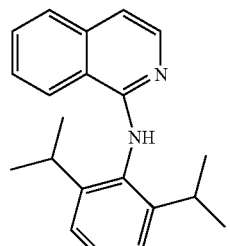

45%, rt, 24 hrs
Cl

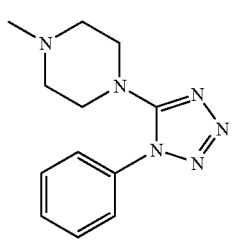

37%, 50° C., 24 hrs
Cl, Sodium tert-butoxide

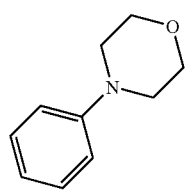

70%, 80° C., 24 hrs,
Cl, Cs$_2$CO$_3$

TABLE 8

EVALUATION OF COMPLEX Ih IN THE KUMADA REACTION: SUBSTRATE SCOPE

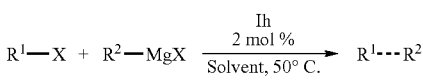

THF:DMI, 2:1

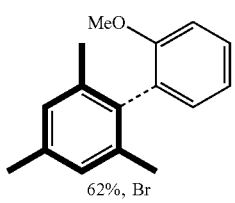

62%, Br

TABLE 8-continued
EVALUATION OF COMPLEX Ih IN THE KUMADA REACTION: SUBSTRATE SCOPE
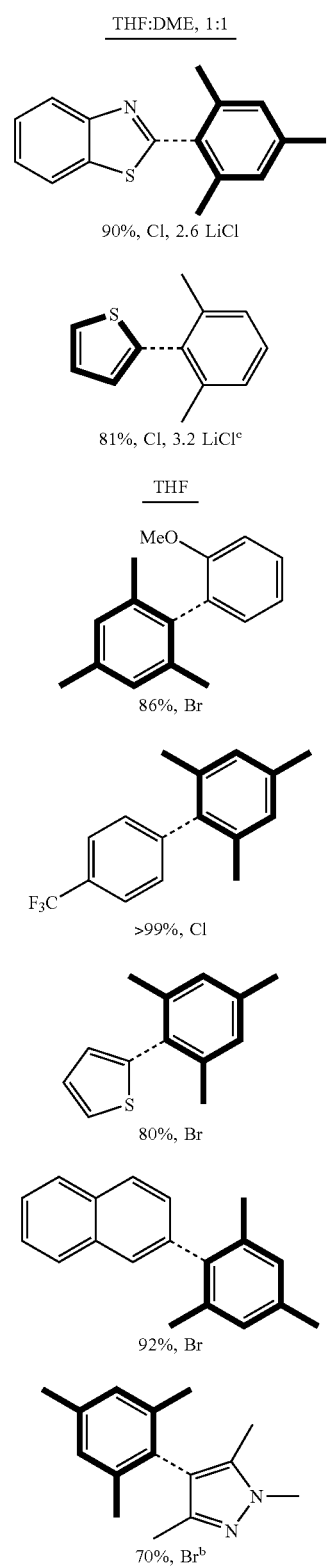
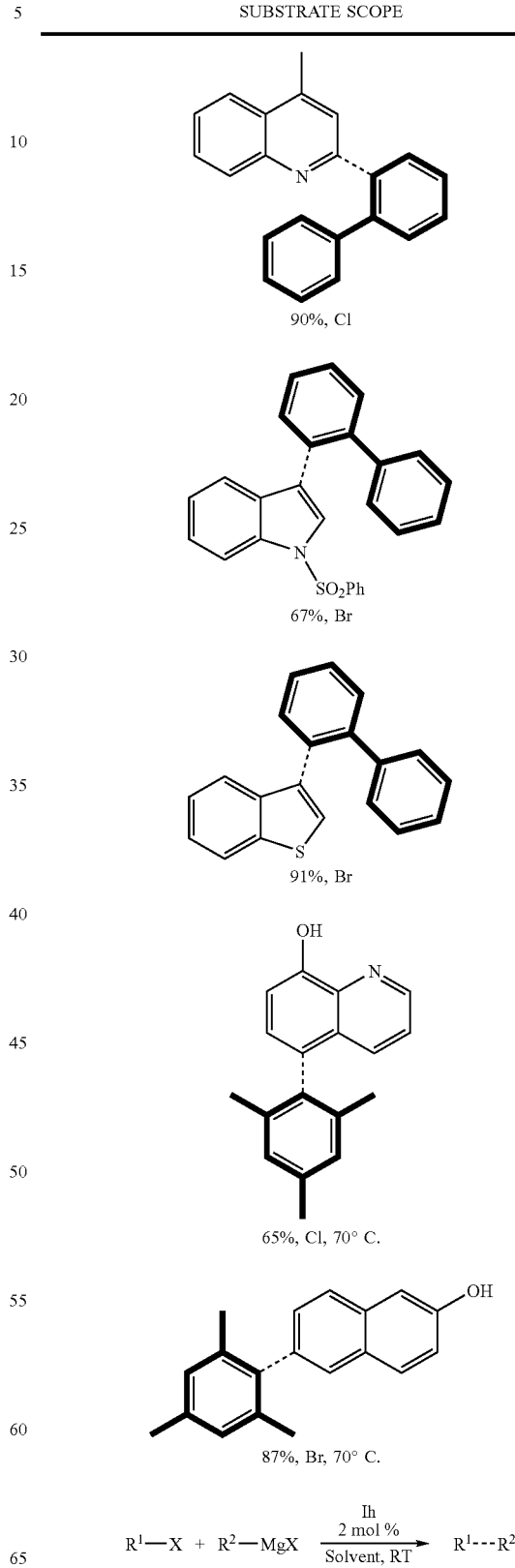
$R^1-X + R^2-MgX \xrightarrow[\text{Solvent, RT}]{\text{Ih} \\ 2 \text{ mol \%}} R^1---R^2$ TABLE 8-continued
EVALUATION OF COMPLEX Ih IN THE KUMADA REACTION: SUBSTRATE SCOPE
THF:DMI, 2:1
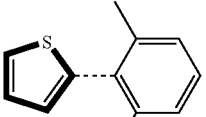
18%, Cl
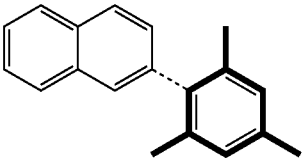
64%, Br
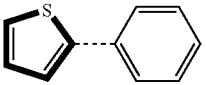
60%, Br
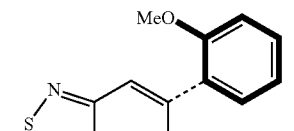
60%, Br
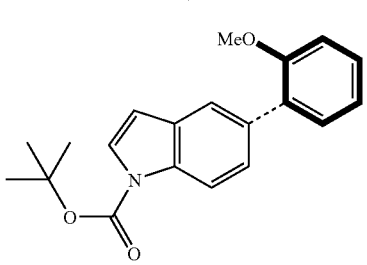
83%, Br
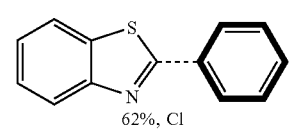
62%, Cl
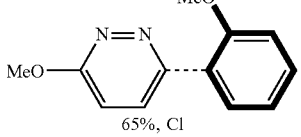
65%, Cl
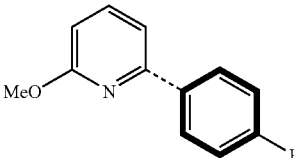
63%, Cl
TABLE 8-continued
EVALUATION OF COMPLEX Ih IN THE KUMADA REACTION: SUBSTRATE SCOPE
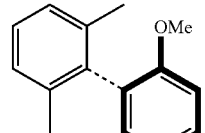
54%, Cl
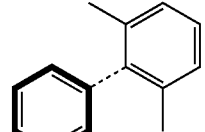
65%, Cl
THF:DME, 1:1
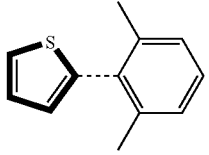
70%, Cl$^c$
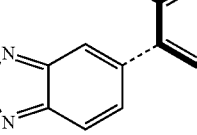
18, 74%, Br
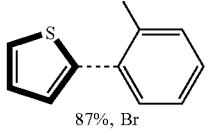
87%, Br
91%, Br
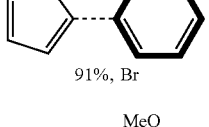
87%, Cl
97%, Cl TABLE 8-continued
EVALUATION OF COMPLEX Ih IN THE KUMADA REACTION: SUBSTRATE SCOPE
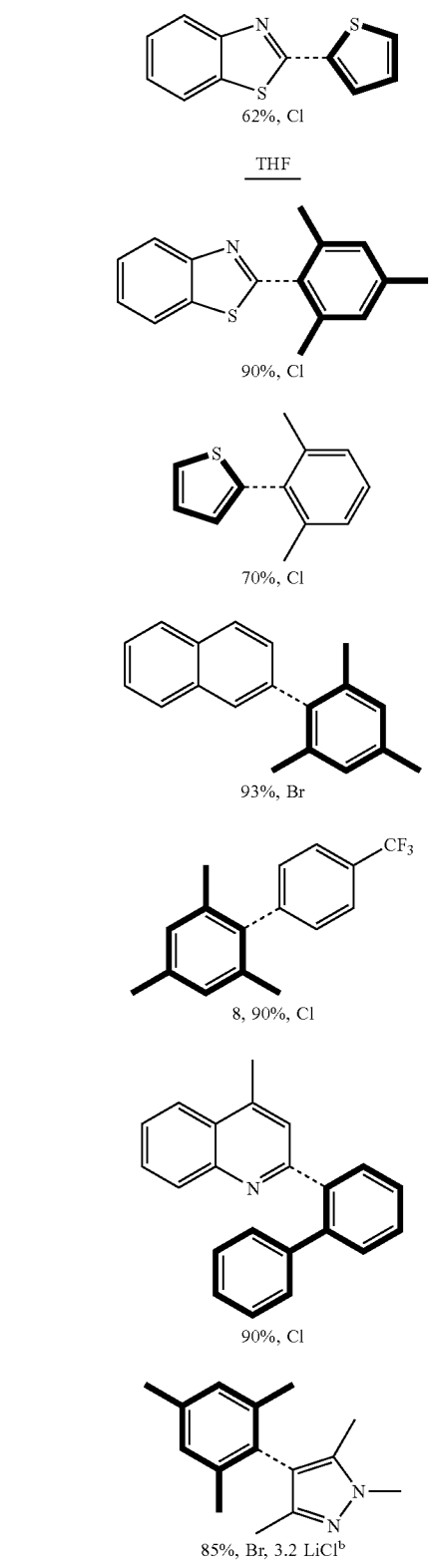
TABLE 8-continued
EVALUATION OF COMPLEX Ih IN THE KUMADA REACTION: SUBSTRATE SCOPE
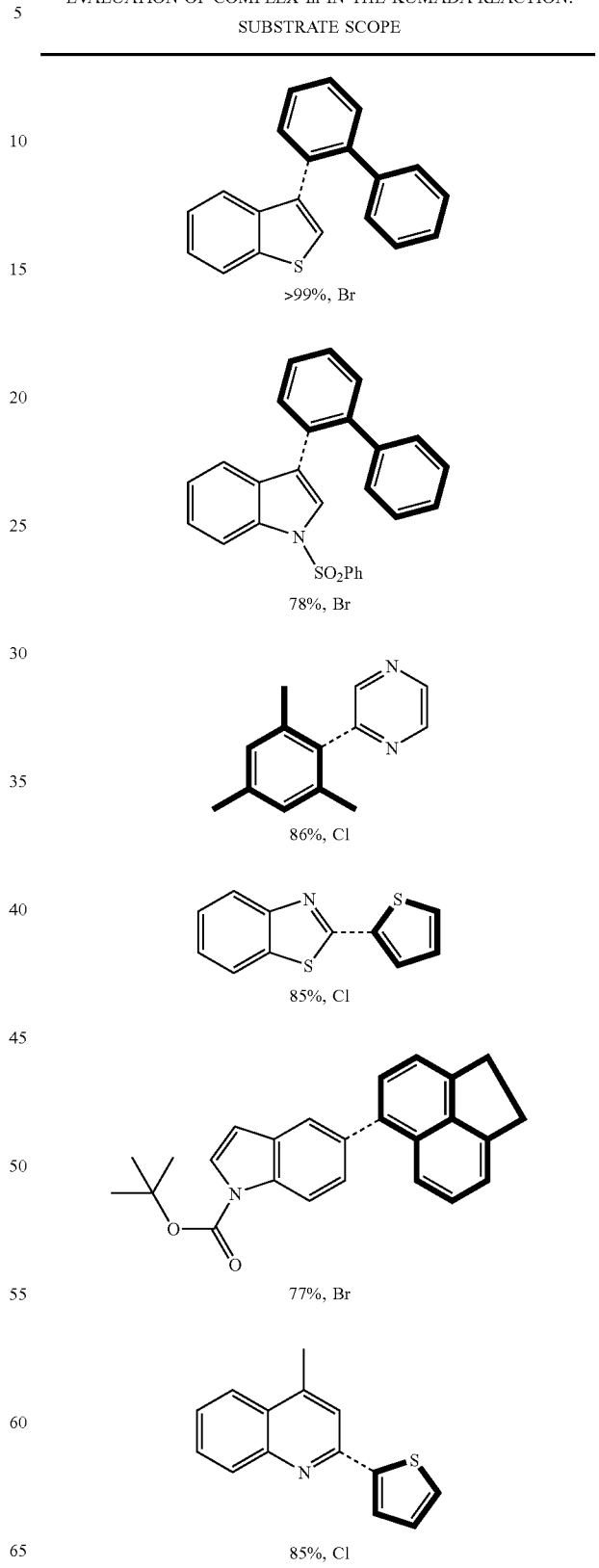

TABLE 8-continued

EVALUATION OF COMPLEX Ih IN THE KUMADA REACTION: SUBSTRATE SCOPE

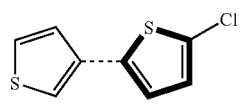

81%, Br

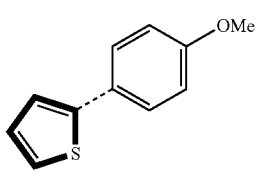

67%, Cl

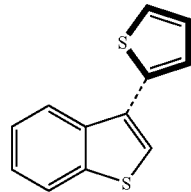

90%, Br

87%, Br

TABLE 8-continued

EVALUATION OF COMPLEX Ih IN THE KUMADA REACTION: SUBSTRATE SCOPE

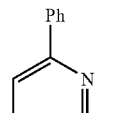

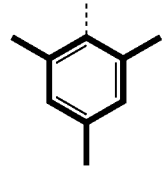

79%, Cl

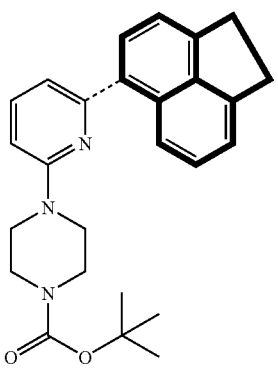

83%, Br

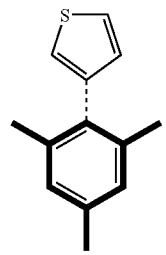

79%, Br

[a]Modifications from the conditions above are outline immediately below the product.
[b]Reaction conducted using IK (2 mol %).
[c]Yielded 90% when the reaction was performed with IK.

TABLE 9

BIS-PINICOL BORANE REACTION RESULTS

| Entry | Product | Catalyst mol % | Solvent | Time | Yield [%][a] |
|---|---|---|---|---|---|
| 1 | phenyl-Bpin | 2 | DMSO | 20 | 52 |
| 2 | phenyl-Bpin | 3 | DMSO | 17 | 60 |
| 3 | phenyl-Bpin | 3 | DMF | 17 | 64 |
| 4 | phenyl-Bpin | 2 | DMSO | 15 min | 36 |
| 5 | 4-NC-C₆H₄-Bpin | 3 | DMSO | 20 | 58 |
| 6 | 2-NC-C₆H₄-Bpin | 3 | DMSO | 20 | 58 |
| 7 | 4-O₂N-C₆H₄-Bpin | 3 | DMSO | 19 | 65 |

TABLE 9-continued

BIS-PINICOL BORANE REACTION RESULTS

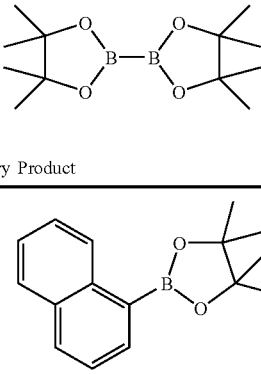

| Entry | Product | Catalyst mol % | Solvent | Time | Yield [%][a] |
|---|---|---|---|---|---|
| 8 | 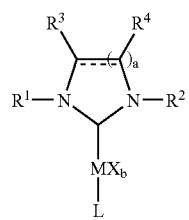 | 3 | DMSO | 42 | 57 |

[a]Yield is reported on material that has been purified by flash chromatography on silica gel.

We claim:

1. A compound of the formula I:

I wherein
- $R^1$ and $R^2$ are independently or simultaneously selected from the group consisting of $C_{1-20}$alkyl, $C_{3-20}$cycloalkyl, aryl and heteroaryl, said latter 4 groups being optionally substituted and/or one or more of the $CH_2$ groups in $C_{1-20}$alkyl and/or $C_{3-20}$cycloalkyl is optionally replaced with a heteroatom selected from the group consisting of O, S, and $NR^5$;
- $R^3$ and $R^4$ are independently or simultaneously selected from the group consisting of H, halo, $C_{1-20}$alkyl, $OC_{1-20}$alkyl, $C_{3-20}$cycloalkyl, $OC_{3-20}$cycloalkyl, aryl, O-aryl, heteroaryl and O-heteroaryl, said latter 8 groups being optionally substituted and/or one or more of the $CH_2$ groups in $C_{1-20}$alkyl, $OC_{1-20}$alkyl, $C_{3-20}$cycloalkyl and/or $OC_{3-20}$cycloalkyl is optionally replaced with a heteroatom selected from the group consisting of O, S, and $NR^5$; or
  - $R^3$ and $R^4$ are linked to form an optionally substituted 4 to 12-membered ring system which optionally contains one or more heteroatoms selected from the group consisting of O, S, and $NR^5$;
- $R^5$ is selected from the group consisting of H and $C_{1-6}$alkyl;
- ----- is a single or a double bond;
- a is 1, 2 or 3;
- M is a transition metal;
- b is an integer representing the number of the anionic ligands X required to fulfill the valency requirements of M;
- X is an anionic ligand and when b is greater than 1, each X may be the same or different;
- L is a 5- to 6-membered optionally substituted N-containing aromatic heterocycle coordinated to M through N, which is optionally benzofused, and/or optionally contains one or more other heteroatoms selected from the group consisting of O, S, and $NR^5$, and/or one or more of the optional substituents on the N-containing aromatic heterocycle is bonded to M in place of one or more X; or
- L is $R^6$—CH=CH—$R^7$ in which $R^6$ and $R^7$ are independently or simultaneously selected from the group consisting of $C_{1-20}$alkyl, $OC_{1-20}$alkyl, $C_{3-20}$cycloalkyl, $OC_{3-20}$cycloalkyl, aryl, O-aryl, heteroaryl and O-heteroaryl, said latter 8 groups being optionally substituted;
- one or more of the carbons of the alkyl and cycloalkyl groups of $R^6$ and $R^7$ are optionally replaced with —C(O)—, —C(O)$NR^5$— and —C(O)O—;
- aryl is an optionally substituted mono- or polycyclic aromatic radical containing from 6 to 14 carbon atoms;
- heteroaryl is a mono- or polycyclic heteroaromatic radical containing from 5 to 14 atoms, of which 1 to 5 atoms may be a heteroatom selected from the group consisting of S, O, N and $NR^5$; and
- optionally substituted means that one or more of the hydrogens on the group are optionally replaced with halo, OH, $C_{1-6}$alkyl, $OC_{1-6}$alkyl, fluoro-substituted $C_{1-6}$alkyl, fluoro-substituted $OC_{1-6}$alkyl, aryl or aryl that is substituted with 1-5 substituents independently or simultaneously selected from the group consisting of fluoro, $C_{1-4}$alkyl, $OC_{1-4}$alkyl, fluoro-substituted $C_{1-4}$alkyl and fluoro-substituted $OC_{1-4}$alkyl.

2. The compound according to claim 1, wherein $R^1$ and $R^2$ are independently or simultaneously optionally substituted $C_{3-10}$cycloalkyl or aryl.

3. The compound according to claim 2, wherein $R^1$ and $R^2$ are independently or simultaneously selected from the group consisting of cyclopropane, adamantyl and phenyl.

4. The compound according to claim 1, wherein $R^3$ and $R^4$ are H.

5. The compound according to claim 1, wherein $R^3$ and $R^4$ are linked to form an optionally substituted 6-membered ring system.

6. The compound according to claim 1, wherein the optional substituents are selected from the group consisting of F, methyl, ethyl, isopropyl, $OCH_3$, $CF_3$, $OCF_3$, phenyl and phenyl that is substituted with 1-3 substituents independently or simultaneously selected from the group consisting of F, methyl, OCH$_3$, CF$_3$ and OCF$_3$.

7. The compound according to claim 6, wherein phenyl is further substituted with OC$_{1-6}$alkyl.

8. The compound according to claim 1, wherein a is 1.

9. The compound according to claim 1, wherein M is selected from the group consisting of Fe, Ru, Os, Co, Rh, Ir, Ni, Pd and Pt.

10. The compound according to claim 9, wherein M is selected from the group consisting of Fe, Ru, Rh, Ir, Pd and Pt.

11. The compound according to claim 10, wherein M is Pd or Pt.

12. The compound according to claim 1, wherein L is selected from the group consisting of pyridine, pyriazine, imidazole, quinoxaline and quinoline, all of which are optionally substituted.

13. The compound according to claim 12, wherein L is selected from the group consisting of

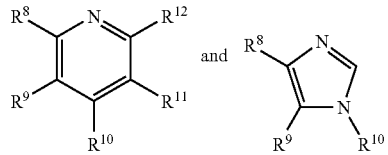

in which R$^8$, R$^9$, R$^{10}$, R$^{11}$ and R$^{12}$ are independently or simultaneously selected from the group consisting of H, halo, OH, C$_{1-6}$alkyl, OC$_{1-6}$alkyl, C$_{3-7}$cycloalkyl, OC$_{3-7}$cycloalkyl, fluoro-substituted C$_{1-6}$alkyl, fluoro-substituted OC$_{1-6}$alkyl, aryl or aryl that is substituted with 1-5 substituents independently or simultaneously selected from the group consisting of fluoro, C$_{1-4}$alkyl, OC$_{1-4}$alkyl, fluoro-substituted C$_{1-4}$alkyl and fluoro-substituted OC$_{1-4}$alkyl.

14. The compound according to claim 13, wherein R$^8$, R$^9$, R$^{10}$, R$^{11}$ and R$^{12}$ are independently or simultaneously selected from the group consisting of H, halo, C$_{1-10}$alkyl, C$_{3-17}$cycloalkyl and aryl.

15. The compound according to claim 14, wherein R$^8$, R$^9$, R$^{10}$, R$^{11}$ and R$^{12}$ are independently or simultaneously selected from the group consisting of H, Br, Cl, C$_{1-6}$alkyl, fluoro-substituted C$_{1-6}$alkyl, C$_{5-6}$cycloalkyl and phenyl.

16. The compound according to claim 15, wherein R$^8$, R$^9$, R$^{10}$, R$^{11}$ and R$^{12}$ are independently or simultaneously selected from the group consisting of H, CH$_3$, CF$_3$, Br, Cl and phenyl.

17. The compound according to claim 13, wherein R$^8$ or R$^{12}$ on the N-containing aromatic heterocycle is bonded to M in place of one or more X.

18. The compound according to claim 13, wherein L is

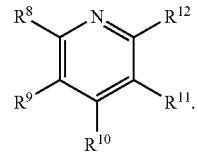

19. The compound according to claim 1, wherein X is F, Br, Cl, I or OC(O)CH$_3$.

20. The compound according to claim 19, wherein X is Cl or Br.

21. The compound according to claim 1, selected from

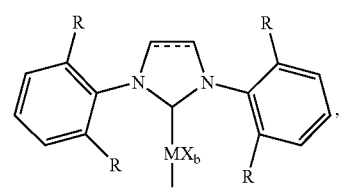

Ia

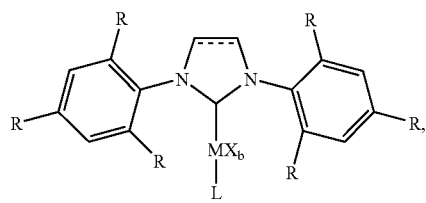

Ib

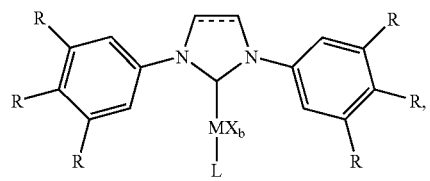

Ic

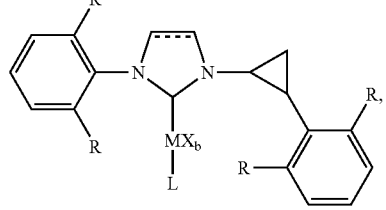

Id

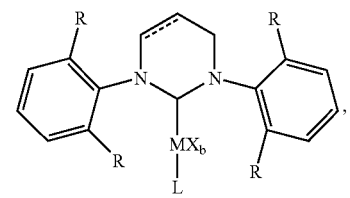

Ie

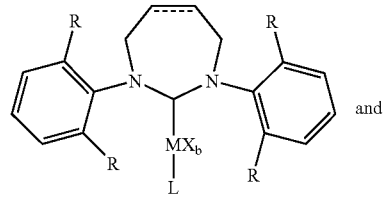

If

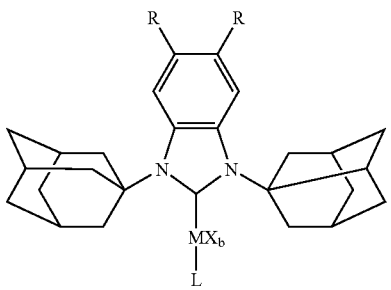

Ig wherein R is H, methyl, ethyl, isopropyl, OCH$_3$, CF$_3$, OCF$_3$ or F, and M, X, b, ----and L are as defined in claim 1.

22. The compound according to claim 1, selected from
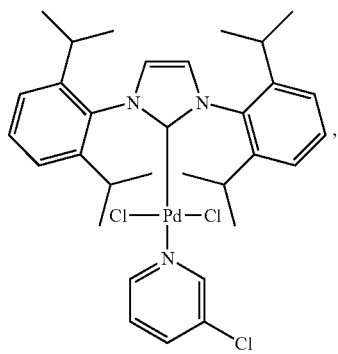
1h
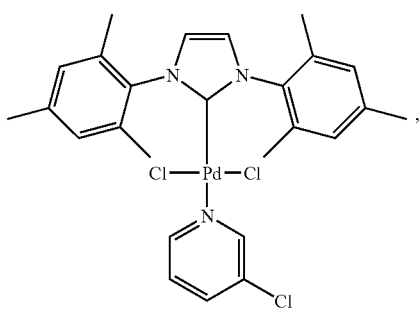
1i
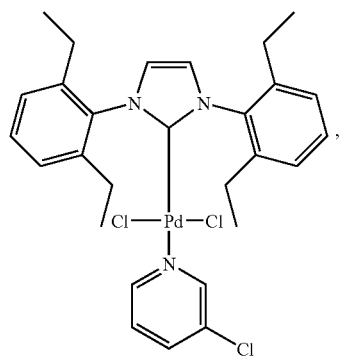
1j
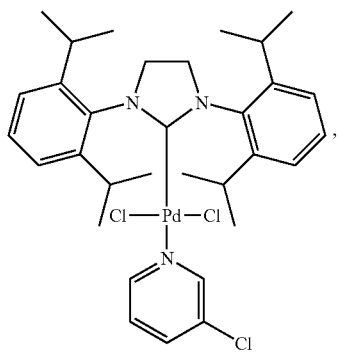
1k
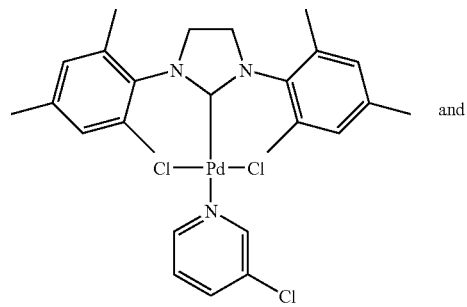
1m
and
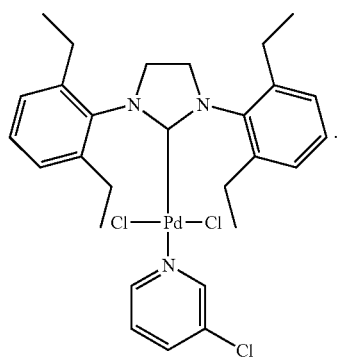
1n
23. The compound according to claim 1 which is:
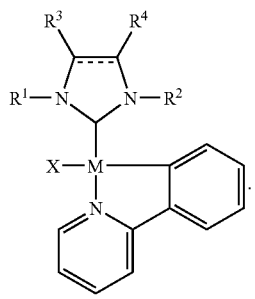
1o
wherein $R^1$, $R^2$, $R^3$, $R^4$, M, ----- and X are as defined in claim 1.
24. The compound according to claim 1 which is:
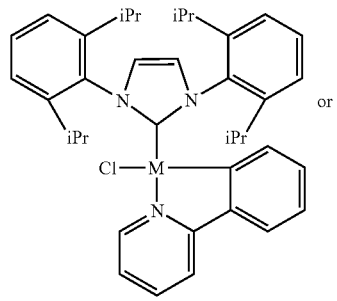
1p
or -continued

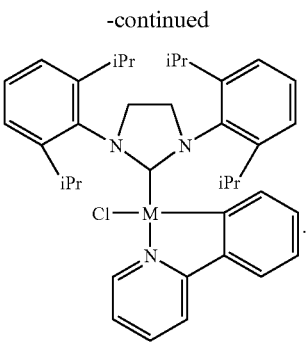

Iq

25. The compound according to claim 1, wherein the compound is attached to a solid support.

26. A method of preparing a compound of formula I according to claim 1, the method comprising:
combining a salt of an N-heterocyclic carbene, a ligand L and a metal salt $MX_b$ in the presence of a base to form a reaction mixture; and
separating the compound of formula I formed in the reaction mixture;
wherein the N-heterocyclic carbene is

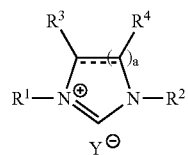

wherein $R^1$ to $R^4$, M, b and L are as defined in claim 1 and Y is any suitable anion.

27. The method according to claim 26, wherein Y is selected from the group consisting of $F^-$, $Cl^-$, $Br^-$, $I^-$ and $PF_6^-$.

28. The method according to claim 26, wherein the base is $Cs_2CO_3$, $K_2CO_3$, $Na_2CO_3$, $K_3PO_3$, $CaCO_3$ or NaOAc.

29. The method according to claim 26, wherein the reaction mixture is at a temperature of about 20 to 90° C.

30. The method according to claim 26, wherein the reaction mixture further comprising a solvent.

31. The method according to claim 26, wherein the compound of formula I is separated from the reaction mixture by purification techniques selected from the group consisting of filtration, recrystallization, extraction, chromatography and combinations thereof.

32. A method for performing a metal-catalyzed cross-coupling reaction comprising: contacting suitable cross-coupling substrates with a compound of formula I according to claim 1, under conditions for the formation of cross-coupling product, to form a reaction mixture; and, optionally separating the cross-coupling product from the reaction mixture; wherein the compound of formula I is converted to an active catalyst under suitable reaction conditions in the reaction mixture.

33. The method according to claim 32, wherein the metal-catalyzed cross-coupling reaction is a Negishi coupling reaction, a Heck coupling reaction, a Suzuki coupling reaction, a Hiyama coupling reaction, a Sonogashira coupling reaction, a Stille coupling reaction, a Kumada coupling reaction, a Buchwald-Hartwig amination reaction, an allyl substitution reaction, an enolate arylation reaction, a hydroformylation reaction, a carbonylation reaction, a hydrosilylation reaction or a boronylation reaction.

* * * * *